(12) United States Patent
Harks et al.

(10) Patent No.: US 10,335,192 B2
(45) Date of Patent: Jul. 2, 2019

(54) APPARATUS FOR DETERMINING A PROPERTY OF AN OBJECT USING ULTRASOUND SCATTER

(75) Inventors: Godefridus Antonius Harks, Eindhoven (NL); Fei Zuo, Eindhoven (NL); Szabolcs Deladi, Eindhoven (NL); Steven Antonie Willem Fokkenrood, Eindhoven (NL); Nenad Mihajlovic, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 664 days.

(21) Appl. No.: 13/643,116

(22) PCT Filed: Apr. 15, 2011

(86) PCT No.: PCT/IB2011/051640
§ 371 (c)(1),
(2), (4) Date: Oct. 24, 2012

(87) PCT Pub. No.: WO2011/135482
PCT Pub. Date: Nov. 3, 2011

(65) Prior Publication Data
US 2013/0041259 A1 Feb. 14, 2013

(30) Foreign Application Priority Data

Apr. 28, 2010 (EP) .................................... 10161318
Aug. 17, 2010 (EP) .................................... 10173025

(51) Int. Cl.
*A61B 8/00* (2006.01)
*A61B 8/08* (2006.01)
(Continued)

(52) U.S. Cl.
CPC ........ *A61B 17/3403* (2013.01); *A61B 8/0833* (2013.01); *A61B 8/12* (2013.01);
(Continued)

(58) Field of Classification Search
USPC ............................................... 604/22
See application file for complete search history.

(56) References Cited

U.S. PATENT DOCUMENTS 7,025,765 B2   4/2006   Balbierz et al.
7,918,850 B2   4/2011   Govari et al.
(Continued)

FOREIGN PATENT DOCUMENTS

CN   101119767 A   2/2008
CN   101453942 A   6/2009
(Continued)

OTHER PUBLICATIONS

Linker et al. Analysis of backscattered ultrasound from normal and diseased arterial wall. International Journal of Cardiac Imaging. 4:177-185. 1989.*
(Continued)

*Primary Examiner* — Amelie R Gillman

(57) ABSTRACT

A monitoring apparatus for monitoring an ablation procedure applied to an object comprises an ultrasound signal providing unit for providing an ultrasound signal. The ultrasound signal is produced by sending ultrasound pulses out to the object, by subsequently receiving dynamic echo series after the ultrasound pulses have been reflected by the object, and finally by generating the ultrasound signal depending on the received dynamic echo series, whereby ultrasound scattering properties of the object are determined that represent blood perfusion. The monitoring apparatus further comprises an ablation depth determination unit for determining an ablation depth from the provided ultrasound signal.

13 Claims, 19 Drawing Sheets

(51) Int. Cl.
| | |
|---|---|
| A61B 8/12 | (2006.01) |
| A61B 6/00 | (2006.01) |
| A61B 17/00 | (2006.01) |
| A61B 17/34 | (2006.01) |
| A61B 34/00 | (2016.01) |
| A61B 90/00 | (2016.01) |
| A61B 18/02 | (2006.01) |
| A61B 18/14 | (2006.01) |
| A61B 18/00 | (2006.01) |
| A61B 18/18 | (2006.01) |
| A61B 34/30 | (2016.01) |
| A61B 34/20 | (2016.01) |

(52) U.S. Cl.
CPC ............. *A61B 34/71* (2016.02); *A61B 90/37* (2016.02); *A61B 6/503* (2013.01); *A61B 6/504* (2013.01); *A61B 8/0891* (2013.01); *A61B 8/445* (2013.01); *A61B 8/4472* (2013.01); *A61B 8/486* (2013.01); *A61B 18/0206* (2013.01); *A61B 18/1492* (2013.01); *A61B 2017/00053* (2013.01); *A61B 2017/00106* (2013.01); *A61B 2017/3413* (2013.01); *A61B 2018/00577* (2013.01); *A61B 2018/0212* (2013.01); *A61B 2018/1861* (2013.01); *A61B 2034/2051* (2016.02); *A61B 2034/2065* (2016.02); *A61B 2034/301* (2016.02); *A61B 2090/374* (2016.02); *A61B 2090/376* (2016.02); *A61B 2090/3762* (2016.02); *A61B 2090/3784* (2016.02); *A61B 2217/007* (2013.01)

(56) References Cited

U.S. PATENT DOCUMENTS

| | | |
|---|---|---|
| 8,146,603 B2 | 4/2012 | Thapliyal et al. |
| 8,320,652 B2 | 11/2012 | Cocosco et al. |
| 2004/0030227 A1 | 2/2004 | Littrup et al. |
| 2005/0283074 A1 | 12/2005 | Jackson et al. |
| 2007/0208327 A1* | 9/2007 | Rosemberg .......... A61B 8/0833 606/11 |
| 2007/0239007 A1* | 10/2007 | Silverman et al. ........... 600/437 |
| 2008/0154131 A1 | 6/2008 | Lee et al. |
| 2008/0253529 A1 | 10/2008 | Boyden et al. |
| 2009/0093807 A1 | 4/2009 | Hyde et al. |
| 2010/0160768 A1* | 6/2010 | Marrouche ............ A61B 6/503 600/420 |
| 2011/0092817 A1* | 4/2011 | Cloutier et al. .............. 600/437 |
| 2013/0041259 A1 | 2/2013 | Harks et al. |

FOREIGN PATENT DOCUMENTS

| | | |
|---|---|---|
| CN | 101500502 A | 8/2009 |
| JP | 1990215448 A | 8/1990 |
| JP | 2007301035 A | 11/2007 |
| TW | 200732011 A | 9/2007 |
| WO | 9501126 A1 | 1/1995 |
| WO | WO2006064495 | 6/2006 |
| WO | 2006087649 A1 | 8/2006 |
| WO | 2011135482 A1 | 11/2011 |

OTHER PUBLICATIONS

Salgaonkar et al. Passive cavitation imaging with ultrasound arrays. J Acoust Soc Am. 125(6):3071. Dec. 2009.*
M. Mokhtari-Dizaji et al., "Ultrasound Monitoring of Temperature Change in Liver Tissue During Laser Thermotherapy", Proc. Int. Conf. IEEE EMBS, 2007, pp. 2130-2133.
A.A. Kaczkowski et al., "Noninvasive Measurement of Local Thermal Diffusivity Using Backscattered Ultrasound and Focused Ultrasound Heating", Ultrasound in Medicine and Biology, 34 (9), Sep. 2008, pp. 1449-1464.
Miller Institute Newsletter, Miller Fellow Focus: Tom Hunt, Fall, 2008, University of California, Berkeley.
Cohen Lab, MIT, "Ultrasound Imaging of Tissue Perfusion by Blood", Apr. 21, 2010.
Sigel, B. et al., "Variable Ultrasound Echogenicity in Flowing blood", Science, vol. 218, Dec. 24, 1982, p. 1321-1323.

* cited by examiner

APPARATUS FOR DETERMINING A PROPERTY OF AN OBJECT USING ULTRASOUND SCATTER

FIELD OF THE INVENTION

The invention relates to a property determining apparatus, method and computer program for determining a property of an object. The invention relates further to an object influencing apparatus comprising the property determining apparatus, a corresponding object influencing method and a corresponding object influencing computer program.

BACKGROUND OF THE INVENTION

WO 2006/064495 A1 discloses a method for monitoring heat damage to tissue during a heat ablation procedure. While a certain part of the tissue is ablated, ultrasound images of neighboring parts of the tissue are acquired, and from these ultrasound images a parameter is extracted, which is indicative of a biological response of the neighboring parts of the tissue to heat. In an embodiment, the parameter is the accumulation of bubbles and a damage of the neighboring parts of the tissue is determined based on this parameter. The aim of this monitoring method is the detection of unwanted damages to the neighboring parts of the tissue. The monitoring method monitors therefore a possible damage of the tissue by observing spatial and temporal changes in the ultrasound images and by relating these changes to bubble formation. This monitoring leads to inaccuracies in determining possible damages of the tissue, because bubble formation reflects only high temperature in the tissue, but is not directly linked to the extent of tissue damage.

SUMMARY OF THE INVENTION

It is an object of the present invention to provide a property determining apparatus, wherein a property of an object can be determined with an improved accuracy. It is a further object of the present invention to provide an object influencing apparatus comprising the property determining apparatus and to provide corresponding methods and computer programs.

In a first aspect of the present invention a property determining apparatus for determining a property of an object is presented, wherein the property determining apparatus comprises:
an ultrasound signal providing unit for providing an ultrasound signal produced by
sending an ultrasound pulse out to the object,
receiving echo series from the object, and
generating the ultrasound signal depending on the received echo series,
a scatter determination unit for determining at least one scatter value being indicative of a scatter of the ultrasound pulse by a fluid perfusing the object, wherein the scatter determination unit is adapted to determine the at least one scatter value depending on the ultrasound signal,
a property determination unit for determining a property of the object depending on the at least one scatter value.

Since the scatter determination unit determines at least one scatter value being indicative of a scatter of the ultrasound pulse by the fluid and since the property determination unit is adapted to determine a property of the object depending on the at least one scatter value, a property, which is related to the perfusion by the fluid, can more directly be determined based on the at least one scatter value. Thus, it is not necessary to use a very indirect measure like a detection of bubble formation, which reflects high temperature in tissue, but which is not directly linked to, for example, the extent of tissue damage, for determining a property of the object. This increases the accuracy of determining a property of the object.

The scatter determination unit can be adapted to determine several scatter values, wherein the property determination unit can be adapted to determine the property based on the several scatter values.

The ultrasound signal providing unit can be a storing unit in which the ultrasound signal is stored already, or the ultrasound signal providing unit can be a data receiving unit like a wired or wireless data connection for receiving the measured ultrasound signal. Moreover, the ultrasound signal providing unit can be formed by one or several ultrasound transducers for generating the ultrasound signal, wherein the same ultrasound transducer can send ultrasound pulses and receive echo series, or a first ultrasound transducer can send ultrasound pulses and another, second ultrasound transducer can receive echo series.

The ultrasound signal providing unit is preferentially adapted to provide an ultrasound signal for different times and different depths within the object. The provided ultrasound signal is preferentially an M-mode image.

The object is preferentially an organ of a person or of an animal, wherein the organ is perfused by a bodily fluid like blood. In particular, the object is preferentially the heart, wherein the tissue of the heart is perfused by blood. It is further preferred that the property determining apparatus is adapted to determine a degree of perfusion, in particular, capillary perfusion, of the object by the fluid as the property based on the at least one scatter value. In particular, the property determination unit is adapted to determine which part of the object is perfused and which part of the object is not perfused. Since the at least one scatter value is indicative of a scatter of the ultrasound pulse by the fluid, the degree of perfusion of the object, in particular, whether the object or a part of the object is perfused or not perfused, can be determined based on the at least one scatter value, i.e. if the object is not perfused by fluid, the scatter determination unit can determine a scatter value being indicative of the absence of the fluid, and the property determination unit can determine, for example, that the object is not perfused, and if the object is perfused by fluid, the scatter determination unit can determine a scatter value being indicative of the presence of the fluid, and the property determination unit can determine, for example, that the object is perfused.

It is further preferred that the object is a biological object like the heart or another organ comprising tissue, wherein the property determination unit is adapted to determine whether a part of the tissue comprises ablated tissue or non-ablated tissue based on the at least one scatter value as the property of the object. In particular, the property determination unit is adapted to determine which part of the tissue is ablated and which part of the tissue is non-ablated. By ablation the perfusion of the object can be modified, wherein the modification of the perfusion can modify the scattering of the ultrasound pulse by the fluid and, thus, the at least one scatter value. The modification of the at least one scatter value can therefore be used for determining the degree of ablation. For instance, by calibration measurements it can be determined which scatter values, or which changes of scatter values after an ablation procedure has been started, correspond to which degrees of ablation, wherein the scatter values are determined, while the degree of ablation is known. These determined scatter values can be regarded as calibration values, wherein the calibration values can then be used for determining the degree of ablation depending on actually determined scatter values.

A means for enhancing the perfusion through the tissue can be applied to the tissue. Such a means is, for example, a vasodilator agent like isoproterenol. If the perfusion is enhanced, differences in the scattering of the ultrasound pulse by ablated tissue and the scattering of the ultrasound pulse by non-ablated tissue can be increased, because the perfusion of non-ablated tissue and the corresponding scattering by the fluid of the non-ablated tissue will be increased, whereas, because ablated tissue is not perfused or only a little perfused, scattering in the region of the ablated tissue will not be increased or only a little increased. This further improves the accuracy of distinguishing between ablated tissue and non-ablated tissue.

It is further preferred that the property determination unit is adapted to determine which part of the tissue is ablated tissue and which part of the tissue is non-ablated tissue and to determine an ablation depth depending on these determined parts of the tissue. Since, after it has been determined which part of the tissue is ablated tissue and which part of the tissue is non-ablated tissue, the spatial distribution of ablated and non-ablated regions within the tissue is known, the ablation depth can easily be determined from the determined ablated and non-ablated parts of the tissue.

It is further preferred that the provided ultrasound signal represents the scattering by the fluid at at least one of a) different depths within the object and b) different times, wherein the ultrasound signal is sampled by sample windows corresponding to the at least one of a) different depths and b) different times, wherein the scatter value determination unit is adapted to determine scatter values for the sample windows, wherein for a respective sample window at least one scatter value is determined based on the part of the ultrasound signal which corresponds to the respective sample window, wherein the property determination unit is adapted to determine a property for the respective sample window based on the at least one scatter value determined for the respective sample window. If, for example, the ultrasound signal is an M-mode image, the M-mode image can be sampled by several sample windows corresponding to certain depth ranges and to certain time ranges. For each of the sample windows at least one scatter value can be determined, wherein for each of the sample windows a property, in particular, whether the tissue within the respective sample window is ablated or non-ablated, can be determined based on the at least one scatter value determined for the respective sample window. This allows monitoring the property over time and in different depths. In particular, the property can be monitored in realtime. For example, the ablation depth may be monitored in realtime.

The sample windows are preferentially overlapping, because then the resolution of determining the property of the object can be increased, without reducing the sample window size. However, the sample windows can also be non-overlapping.

It is further preferred that each of the sample windows corresponds to several ultrasound intensities of the ultrasound signal, wherein the scatter determination unit is adapted to determine at least one scatter value for a sample window depending on a histogram of the ultrasound intensities within the respective sample window. Thus, preferentially for each of the sample windows at least one scatter value is determined depending on a histogram of the ultrasound intensities of the respective sample window. In particular, the scatter determination unit is adapted to determine the at least one scatter value based on at least one of a first-order histogram and a second-order histogram. Also higher-order statistics can be used for determining the at least one scatter value, for example, a Gabor filtering approach can be used for determining the at least one scatter value.

It is further preferred that the scatter determination unit is adapted to determine at least one of the following values as the at least one scatter value: a first-order mean of the first-order histogram, a first-order variance of the first-order histogram, a first-order entropy of the first-order histogram, a second-order entropy of the second-order histogram, a second-order energy of the second-order histogram, a second-order homogeneity of the second-order histogram, a second-order contrast of the second-order histogram, a second-order cluster tendency of the second-order histogram, a second-order shape of the second-order histogram, a second-order correlation of the second-order histogram and a second-order correlation derivative of the second-order histogram.

In an embodiment, each of the sample windows corresponds to several ultrasound intensities of the ultrasound signal, wherein the scatter determination unit is adapted to determine at least one scatter value for a sample window depending on a summation of the ultrasound intensities within the respective sample window. Thus, in addition to or in an alternative to using histogram-based scatter values, also scatter values can be used, which depend on a summation of the ultrasound intensities within the respective sample window. For example, a scatter value can be the sum over all ultrasound intensities within a respective sample window or the sum over products of ultrasound intensities, wherein at least one of the ultrasound intensities of each pair is located within the respective sample window and wherein each product comprises ultrasound intensities which correspond to acquisition times, which are separated by a heart cycle period of the object, if the object is cardiac tissue. If histogram-based scatter values and these summation-based scatter values, which are preferentially not based on a histogram, are used together for determining the property of the object, the accuracy of determining the property of the object can be further improved.

It is further preferred that the property determination unit is adapted to apply a cluster analysis to the sample windows, wherein the sample windows are clustered depending on the at least one scatter value determined for the respective sample window, and to assign properties to the clusters of sample windows. The property determination unit can be adapted to perform a clustering algorithm like a K-means clustering for grouping the scatter values. If for each sample window only a single scatter value has been determined, the clustering algorithm is applied to the single scatter values, and, if for each sample window several scatter values have been determined, the scatter values which have been determined for a single sample window form a multi-dimensional feature vector and the clustering algorithm is applied to the multi-dimensional feature vectors determined for the several sample windows. The clustering algorithm can result in a first cluster of scatter values or multi-dimensional feature vectors, respectively, and, thus, in a corresponding first cluster of sample windows and in a second cluster of scatter values or multi-dimensional feature vectors, respectively and, thus, in a corresponding second cluster of sample windows. The first cluster of sample windows can represent ablated tissue and the second cluster of sample windows can represent non-ablated tissue. Whether a cluster represents ablated or non-ablated tissue can be determined depending on a comparison with a threshold, which can be determined by calibration measurements. Thus, the assignment of properties of the object to the cluster of sample windows can be performed by thresholding. It is also possible that the cluster analysis is firstly applied before ablation is started, leading to a first group of clusters representing non-ablated tissue. Then, the clustering analysis is continuously applied, while the ablation procedure is performed. If the clustering analysis leads to new clusters, which do not belong to the first group of clusters, the property "ablated tissue" can be assigned to these new clusters.

The property determination unit can be adapted to determine the property based on a comparison of the at least one scatter value with at least one threshold value. For example, the ultrasound signal can be sampled by using the above mentioned sample windows and for each sample window at least one scatter value can be determined. It can be defined that, if a scatter value of a sample window is above a threshold value, the tissue, which corresponds to the sample window, is non-ablated, and that, if the scatter value is below the threshold value, the tissue, which corresponds to this sample window, is ablated. If several scatter values have been determined for the same sample window, for each scatter value a threshold value can be provided and for each scatter value it can be determined whether the respective scatter value is above or below the respective threshold value. If, for example, the majority of scatter values of a sample window is above the respective threshold value, it can be defined that the tissue, which corresponds to the sample window, is non-ablated, and if, for example, the majority of scatter values is below the respective threshold value, it can be defined that the tissue, which corresponds to the sample window, is ablated. The one or several thresholds can be determined by, for example, calibration measurements. If for a sample window several scatter values are determined, they can be combined to a multi-dimensional feature vector, i.e. for each sample window a multi-dimensional feature vector can be defined, wherein the multi-dimensional feature vector can be compared with a threshold vector for determining whether the respective sample window corresponds to ablated tissue or to non-ablated tissue.

It is further preferred that the ultrasound signal providing unit is adapted to provide an ultrasound signal produced by using ultrasound waves with a frequency being larger than 10 MHz. The ultrasound waves have preferentially a frequency within a frequency range of 20 to 40 MHz, in particular, a frequency of 30 MHz. Using these relatively high ultrasound frequencies leads to an increased resolution of the ultrasound signal. Since the resolution of the ultrasound signal is increased, patterns in the ultrasound signal, which are caused by scattering of the ultrasound pulse by the fluid, are better recognizable in the ultrasound signal. The extraction of the at least one scatter value from the ultrasound signal and, thus, the quality of the determined property are therefore improved.

It is further preferred that the ultrasound signal providing unit is an ultrasound transducer integrated into a catheter or a needle. This allows using the property determining apparatus to be used for determining a property of, for example, the heart or another organ within a patient, wherein at least the ultrasound transducer can be introduced into the patient.

The property determination unit can also be adapted to determine whether a certain part of the object comprises a vessel, in particular, an artery or a vein, based on the determined at least one scatter value. In particular, the at least one scatter value can be compared with a predefined scatter value range associated with a vessel, wherein, if the at least one scatter value is within the predefined scatter value range, it is determined that the part of the object is a vessel. Also the predefined scatter value range can be determined by calibration measurements, wherein scatter values are determined while the type of the object is known.

In a further aspect of the present invention an object influencing apparatus for influencing an object is presented, wherein the object influencing apparatus comprises an object influencing unit for influencing the object and the property determining apparatus of claim 1. The object influencing apparatus is preferentially an ablation apparatus for ablating an organ of a person or of an animal like the heart. The object influencing unit comprises preferentially an ablation electrode and an energy source, which is connected to the ablation electrode, for heating the object by, for example, radio frequency (RF) energy. Instead of being adapted for performing an RF ablation procedure, the ablation apparatus can also be adapted to perform another kind of ablation like optical ablation, cryoablation, ultrasound ablation, microwave ablation, et cetera.

The object influencing apparatus preferentially comprises a control unit for controlling the object influencing unit, wherein the control unit is adapted to control the object influencing unit depending on the property of the object, which is determined by the property determination unit of the property determining apparatus. As already mentioned above, the property of the object is, for example, the ablation depth. If the object influencing apparatus is an ablation apparatus, which is controlled depending on the ablation depth, the ablation apparatus can be controlled such that a desired ablation depth can be reached. Moreover, it can be determined whether a vessel, in particular, an artery or a vein, is located in front of an ablation electrode as the property of the object. The ablation apparatus can, for example, be controlled such that the ablation is not started or the ablation is stopped, if a vessel has been detected in front of the ablation electrode. In general, by controlling the ablation of the object depending on the determined property of the object, the ablation of the object can be improved.

In a further aspect of the present invention a property determining method for determining a property of an object is presented, wherein the property determining method comprises:
  providing an ultrasound signal produced by
    sending an ultrasound pulse out to the object,
    receiving echo series from the object, and
    generating the ultrasound signal depending on the received echo series,
  determining at least one scatter value being indicative of a scatter of the ultrasound pulse by a fluid perfusing the object, wherein the at least one scatter value is determined depending on the ultrasound signal,
  determining a property of the object depending on the at least one scatter value.

In a further aspect of the present invention an object influencing method for influencing an object is presented, wherein the object influencing method comprises influencing the object and the steps of the property determining method as defined in claim 12. Preferentially, the object influencing method comprises the step of controlling the influencing of the object depending on the determined property of the object. The object influencing method is preferentially an ablation method for ablating an object, wherein preferentially the ablation of the object is controlled depending on the determined property of the object, in particular, depending on the determined ablation depth. The ablation depth can be determined in realtime, in order to control the ablation of the object, while the object is ablated.

In a further aspect of the present invention a property determining computer program for determining a property of an object is presented, wherein the property determining computer program comprises program code means for causing a property determining apparatus as defined in claim 1 to carry out the steps of the property determining method as defined in claim 12, when the computer program is run on a computer controlling the property determining apparatus.

In a further aspect of the present invention an object influencing computer program for influencing an object is presented, wherein the object influencing computer program comprises program code means for causing an object influencing apparatus as defined in claim 11 to carry out the steps of the object influencing method as defined in claim 13, when the computer program is run on a computer controlling the object influencing apparatus.

It shall be understood that the property determining apparatus of claim 1, the object influencing apparatus of claim 10, and the property determining method of claim 11, have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
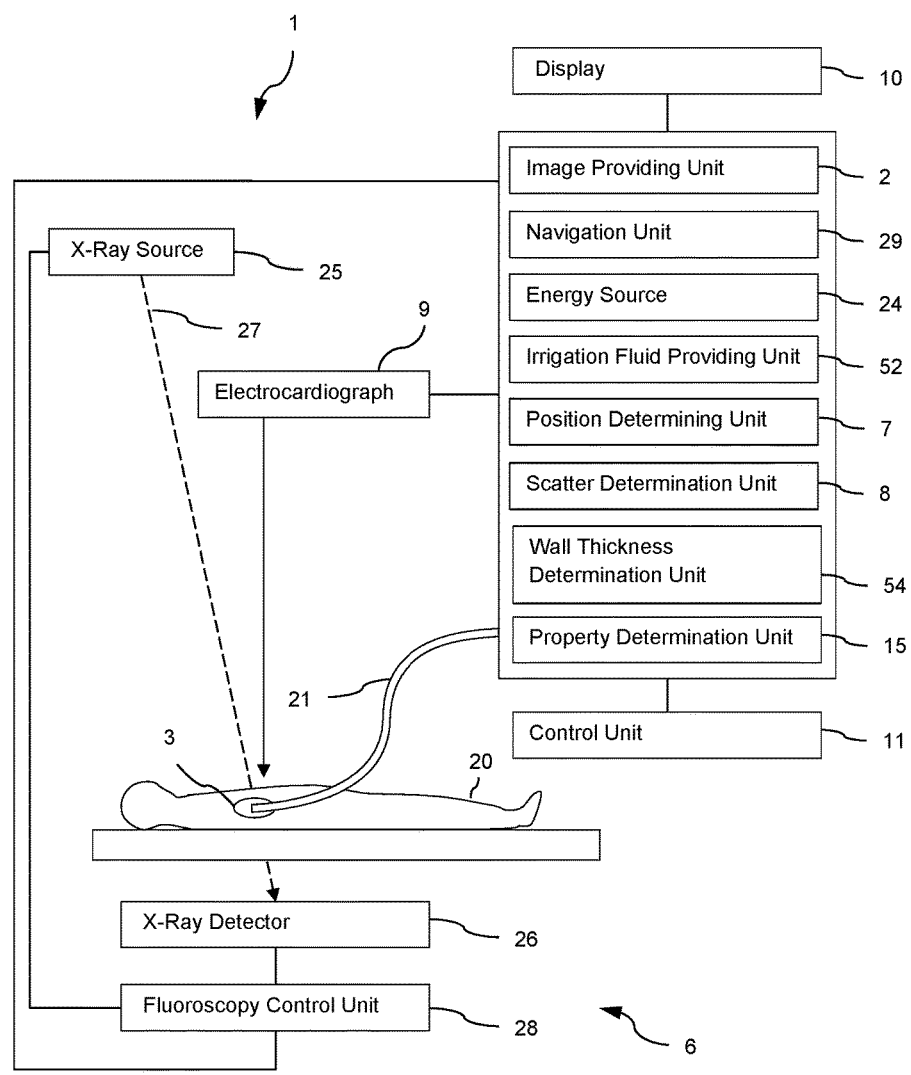
FIG. 1 shows schematically and exemplarily an embodiment of an ablation apparatus for ablating an object.
Figure 2:
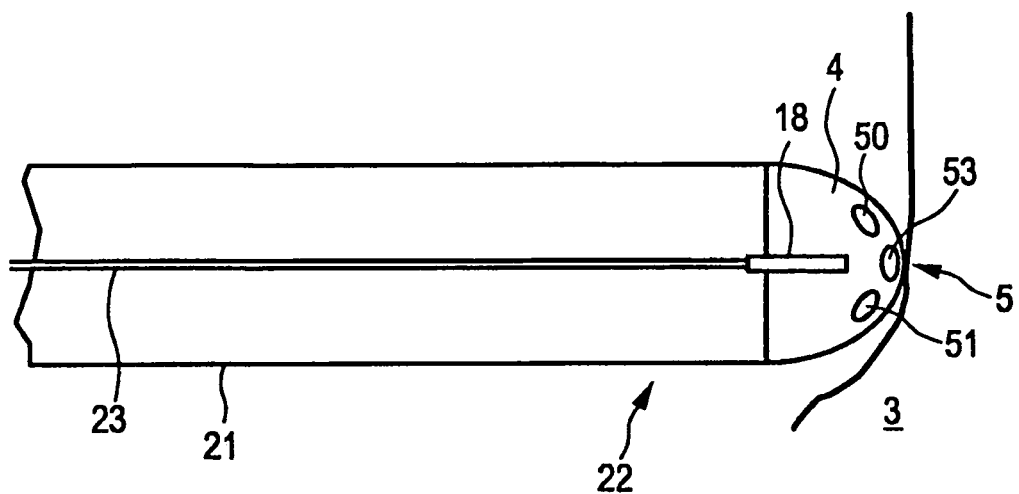
FIG. 2 shows schematically and exemplarily an embodiment of a tip of a catheter of the ablation apparatus.

FIG. 1 shows schematically and exemplarily an ablation apparatus 1 for ablating an object. The ablation apparatus 1 comprises an image providing unit 2 for providing an image of the object 3 being, in this embodiment, a heart of a person 20. The ablation apparatus 1 further comprises a catheter 21 for applying energy to an inner wall of the heart 3. The tip 22 of the catheter 21 is schematically and exemplarily shown in FIG. 2. The catheter tip 22 comprises an ablation electrode 4 for applying energy to the wall of the heart 3 at a location 5 for ablating the wall. The ablation electrode 4 is connected with an energy source 24 via an electrical connection 23 for providing electrical energy at the location 5. Preferentially, the energy source 24, the electrical connection 23 and the ablation electrode 4 are adapted to apply radio frequency (RF) energy to the heart 3 at the location 5. The electrical connection 23 is preferentially a wire. The ablation electrode 4, the electrical connection 23 and the energy source 24 form an object influencing unit.

The catheter tip 22 further comprises an ultrasound signal providing unit 18 for providing an ultrasound signal. The ultrasound signal providing unit 18 is an ultrasound transducer being adapted for sending an ultrasound pulse out to the object, receiving echo series from the object, and generating the ultrasound signal depending on the received echo series. In this embodiment, the ultrasound signal providing unit 18 is adapted to generate an M-mode image which represents the ultrasound properties of the cardiac tissue at the location at different depths and at different times.

The ultrasound transducer 18 is adapted to provide the ultrasound signal, i.e. the M-mode image, by using ultrasound waves with a frequency being larger than 10 MHz. The ultrasound waves have preferentially a frequency within a frequency range of 20 to 40 MHz, in particular, a frequency of 30 MHz.

The catheter tip comprises irrigation openings 50, 51, 53 for allowing an irrigation fluid to leave the catheter tip. The irrigation fluid is provided by an irrigation fluid providing unit 52. The irrigation fluid provided by the irrigation fluid providing unit 52 is introduced into the catheter 21, guided to the catheter tip 22 and leaves the catheter tip 22 through the irrigation openings 50, 51, 53. The irrigation fluid is not only used for irrigation purposes, but also as an acoustical medium defining an acoustical path for the ultrasound pulse and the echo series. The ultrasound pulse and the echo series are preferentially transmitted through the irrigation opening 53. Instead of providing the irrigation opening 53 also an acoustically transparent material like polymethylpentene can be used.

The image providing unit 2 is preferentially adapted to provide an electroanatomic map of the heart 3. In this embodiment, the image providing unit 2 is a storing unit in which the electroanatomic map is stored. The electroanatomic map can be generated by generating a three-dimensional image of the heart 3, for example, by using a computed tomography system, a magnetic resonance imaging system, a nuclear imaging system or an ultrasound imaging system or by impedance, magnetic or electromagnetic-based tracking of the position of the catheter tip, and by measuring the electrical property of the heart at different locations on a wall of the heart, wherein the measured electrical properties are visualized at the respective locations in the three-dimensional image of the heart.

For example, the electroanatomic map can be an activation map reflecting the activation sequence of the anatomical substrate. From this activation map conduction patterns can be derived revealing, for example, zones of late activation or reentrant waves. The information from the activation map can be used to identify ablation targets to which energy should be applied.

The ablation apparatus 1 further comprises a localization unit 6, 7 for localizing the ablation electrode 4 at the different locations. The localization unit comprises an X-ray fluoroscopy system 6 with an X-ray source 25 and an X-ray detector 26. The X-ray source 25 emits an X-ray beam 27 which traverses the heart 3 including the tip 22 of the catheter 21. The X-ray beam, which has traversed the heart 3, is detected by the X-ray detector 26. The X-ray detector 26 generates electrical signals depending on the detected X-ray beam and the electrical signals are used by a fluoroscopy control unit 28 for generating an X-ray projection image. The fluoroscopy control unit 28 is also adapted to control the X-ray source 25 and the X-ray detector 26. The X-ray source 25 and the X-ray detector 26 can be adapted to be rotatable around the patient 20 for allowing the X-ray fluoroscopy system 6 to generate X-ray projection images in different directions. The X-ray fluoroscopy system is, for example, a computed tomography fluoroscopy system or a C-arm fluoroscopy system. The X-ray projection images are provided to a position determination unit 7 for determining the position of the catheter tip 22, in particular, of the ablation electrode 4 and/or the ultrasound transducer 18, within the heart 3. For determining the position of the catheter tip 22 within the heart 3 based on the provided X-ray projection images known position determining methods can be used. For example, the catheter tip 22 can be recognized in the different X-ray projection images, which allows the position determination unit to determine the paths of the X-rays which have caused the respective projection of the catheter tip 22. The position determination unit 7 can be adapted to determine the position of the catheter tip 22 within the heart 3 from the intersection of these paths. Or, a three-dimensional image of the catheter tip 22 within the heart 3 can be generated from the X-ray projection images, for example, by using a backprojection algorithm, wherein the position determination unit 7 can be adapted to determine the position of the catheter tip 22 within the heart 3 by recognizing the catheter tip 22 within the heart 3 in the generated three-dimensional image. The position determination unit 7 can also be adapted to determine the orientation of the catheter tip 22.

In other embodiments, the localization unit can comprise other means like a magnetic resonance imaging system or location sensors at catheter tip 22 for determining the position and optionally also the orientation of the catheter tip 22 within the heart 3. The localization unit can be adapted to allow localizing the catheter tip 22 in realtime.

The ablation apparatus 1 further comprises a navigation unit 29 for allowing the catheter 21, in particular, the catheter tip 22, to be navigated to a desired location within the object 3. The navigation unit 29 can be adapted to allow a user to navigate the catheter 21 completely by hand or semi-automatically depending on a determined position and preferentially orientation of the catheter tip 22. The catheter 22 comprises build-in guiding means (not shown in FIG. 1), which can be controlled by the navigation unit 29. The catheter 29 can, for example, be steered and navigated by the use of steering wires, in order to guide the catheter tip 22 to a desired location within the object 3.

Figure 3:
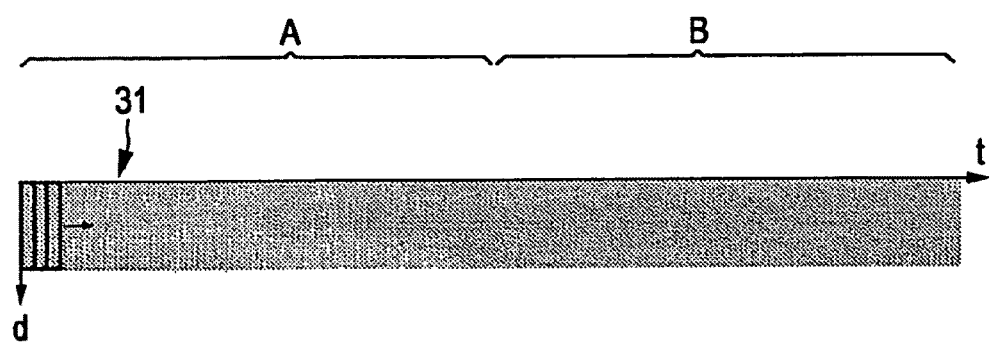
FIG. 3 shows exemplarily an M-mode image of tissue comprising ablated tissue and non-ablated tissue.
Figure 4:
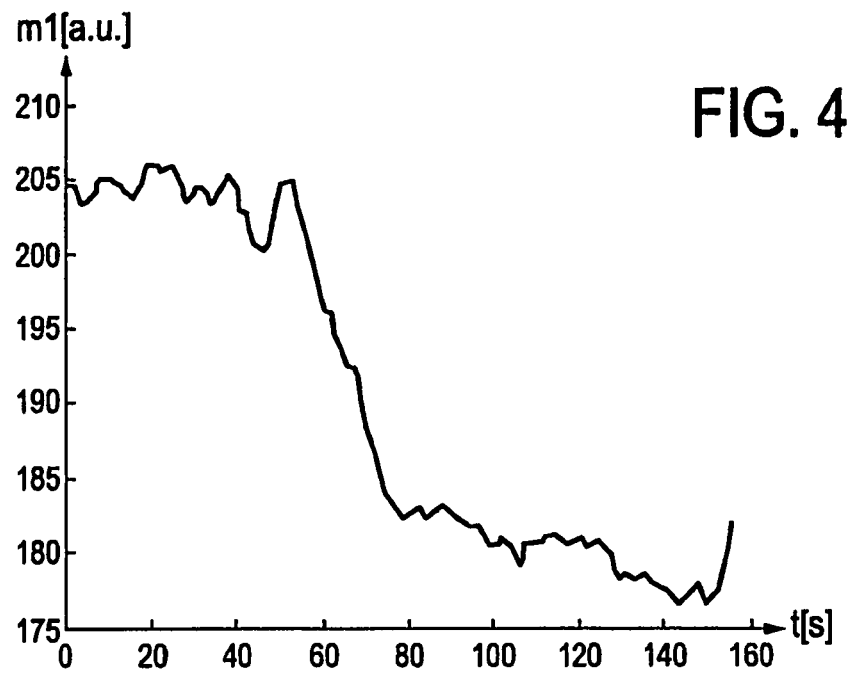
FIGS. 4 to 13 show several scatter values depending on time.
Figure 5:
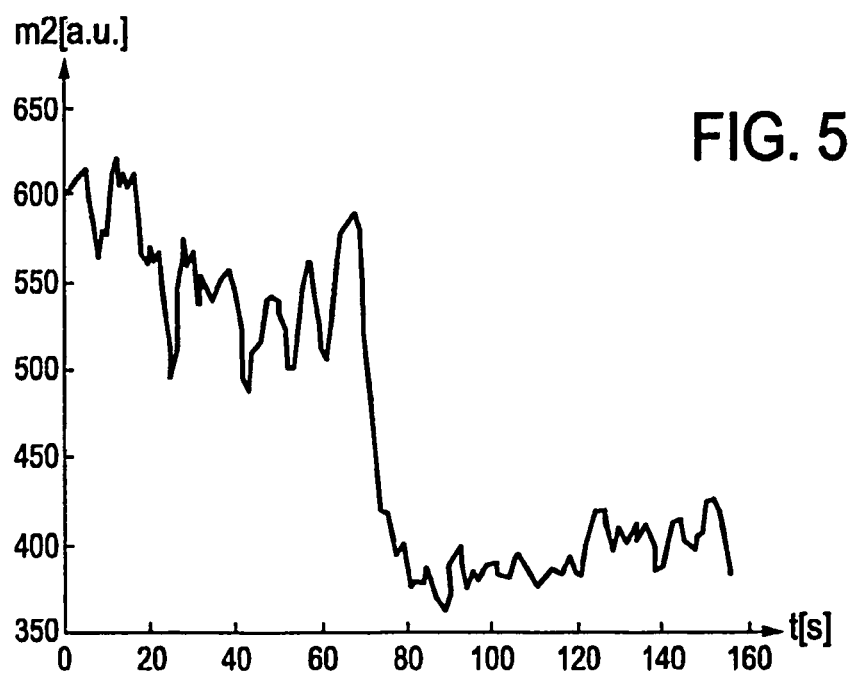
Figure 6:
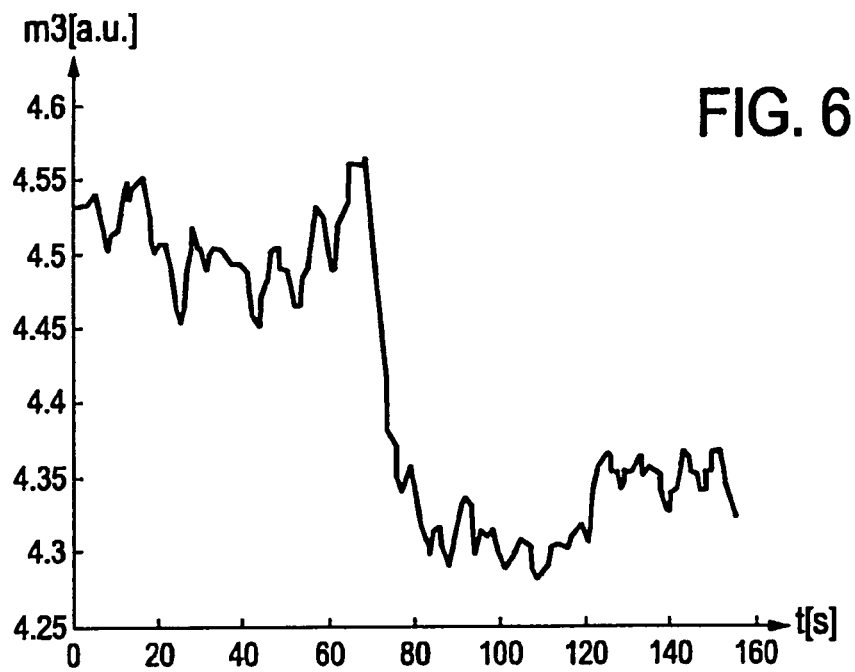
Figure 7:
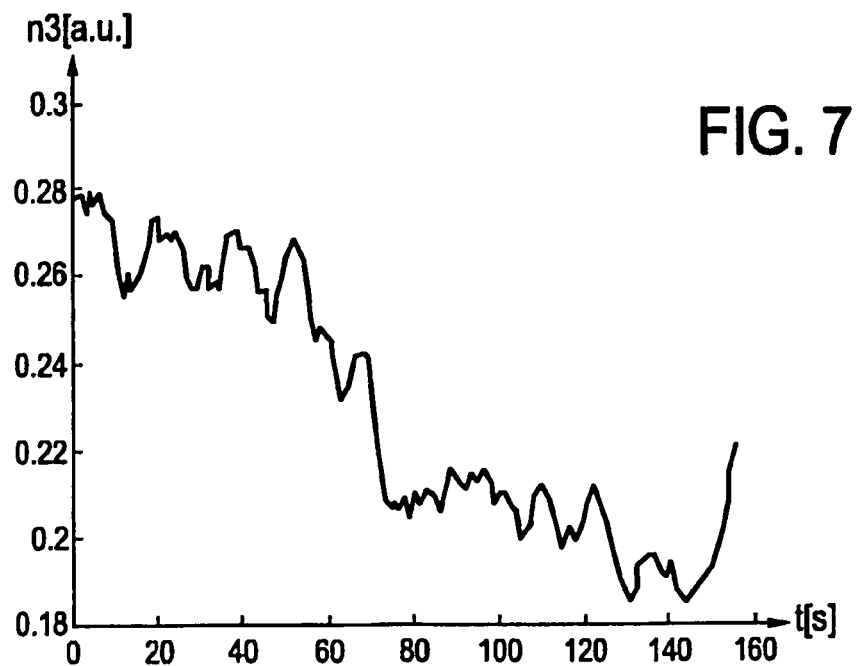
Figure 8:
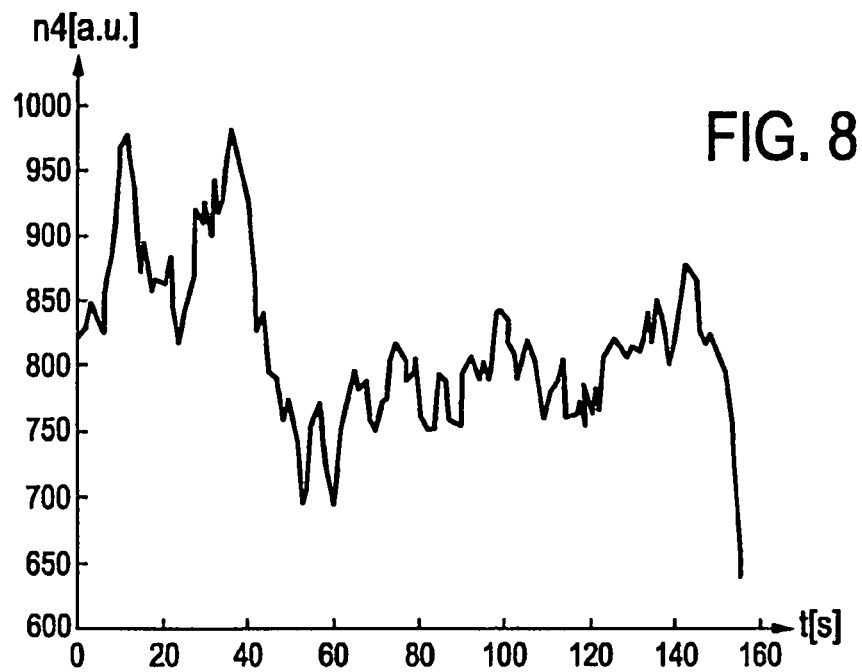
Figure 9:
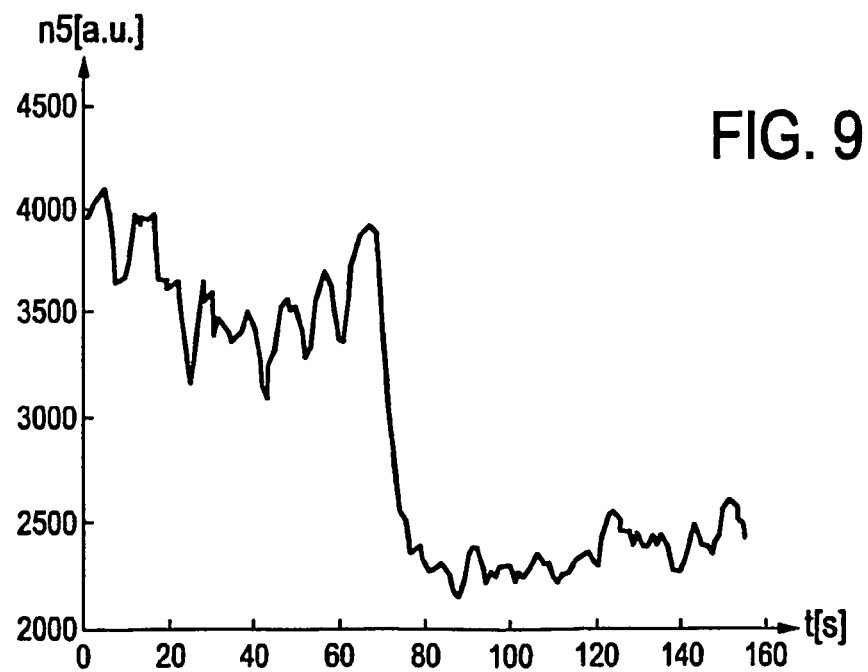
Figure 10:
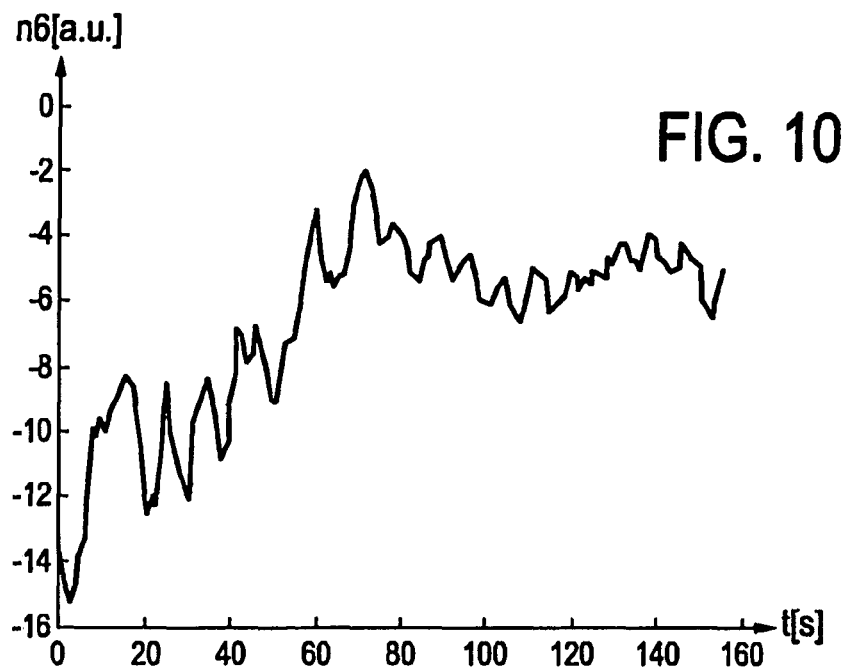
Figure 11:
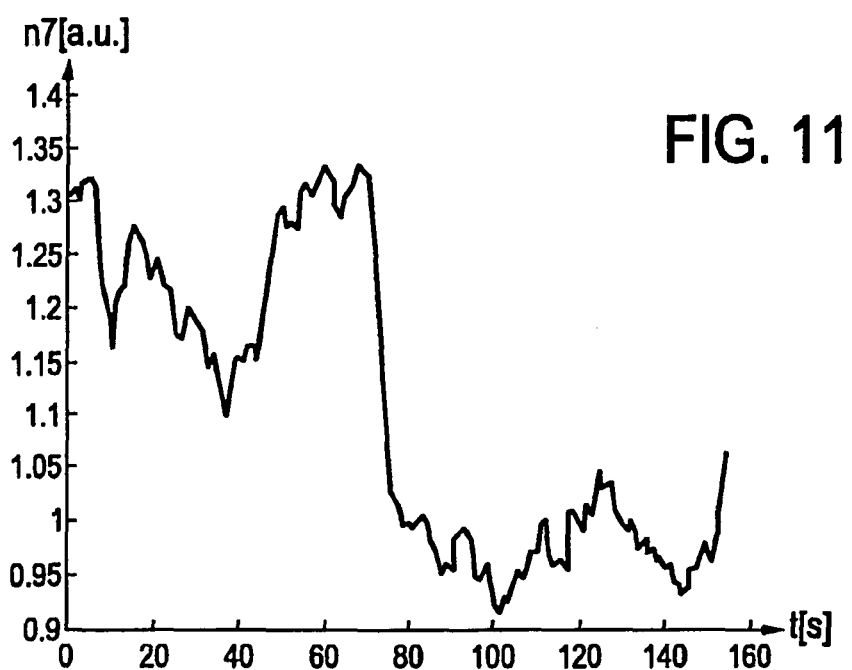
Figure 12:
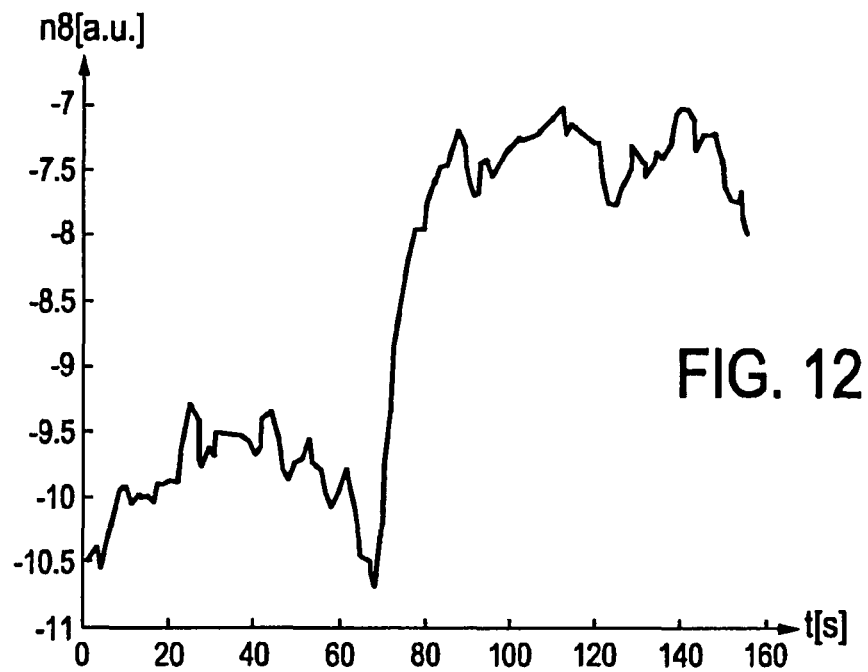
Figure 13:
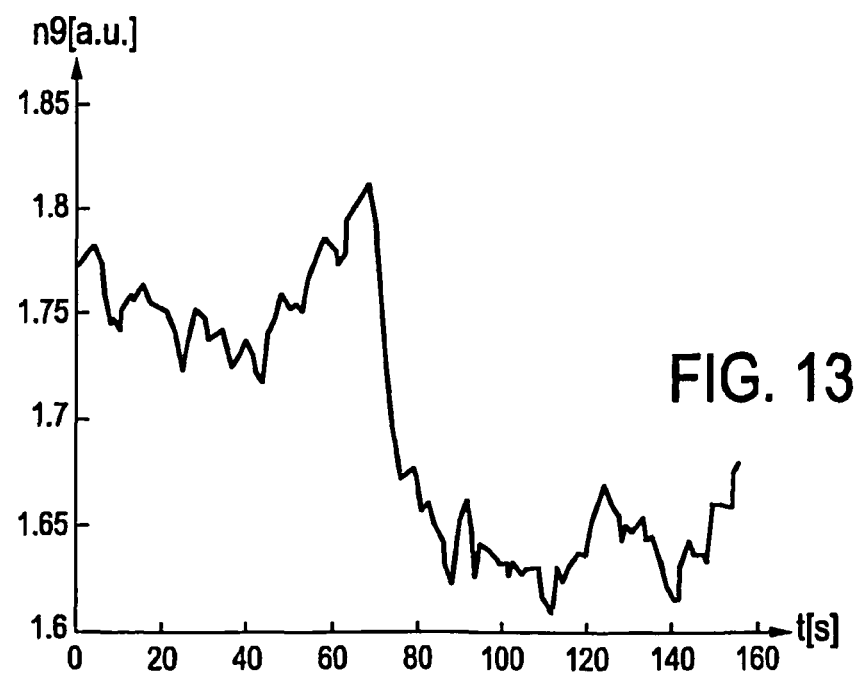

The ablation apparatus 1 further comprises a scatter determination unit 8 for determining at least one scatter value being indicative of a scatter of the ultrasound pulse by blood within cardiac tissue, wherein the scatter determination unit 8 is adapted to determine the at least one scatter value depending on the ultrasound signal. FIG. 3 shows schematically and exemplarily an ultrasound signal 30 being an M-mode image. The M-mode image shows ultrasound intensities of the ultrasound signal depending on different depths d within the tissue depending on the time t. In a first time interval indicated by A the tissue is perfused by blood and in a second time interval indicated by B the tissue is not perfused by blood. The tissue with blood perfusion corresponds to non-ablated tissue and the tissue without blood perfusion corresponds to ablated tissue. The M-mode image is sampled by sample windows 31, which are non-overlapping and which extend along the entire depth range of the M-mode image. The scatter value determination unit 8 is adapted to determine several scatter values for each of the sample windows 31 depending on a histogram of the ultrasound intensities within the respective sample window 31. In particular, the scatter determination unit 8 is adapted to determine the scatter values based on at least one of a first-order histogram and a second-order histogram. However, also higher-order statistics can be used for determining the scatter values, for example, a Gabor filtering approach can be used for determining the at least one scatter value.

The scatter determination unit 8 can be adapted to determine several of the following values as scatter values of a respective sample window 31: a first-order mean $m_1$ of a first-order histogram, a first-order variance $m_2$ of the first-order histogram, a first-order entropy $m_3$ of the first-order histogram, a second-order entropy $n_1$ of a second order-histogram, a second-order energy $n_2$ of the second-order histogram, a second-order homogeneity $n_3$ of the second-order histogram, a second-order contrast $n_4$ of the second-order histogram, a second-order cluster tendency $n_5$ of the second-order histogram, a second order-shape $n_6$ of the second-order histogram, a second-order correlation $n_7$ of the second-order histogram and second-order correlation derivatives $n_8$ and $n_9$ of the second-order histogram.

A first-order histogram is a standard histogram, wherein for different ultrasound intensities, i.e. for different ultrasound intensity bins, the number P(I) of pixels having the intensity I, i.e. located in the respective intensity bin, is determined. The first-order mean $m_1$ of this first-order histogram can be defined by following equation:

$$m_1 = \Sigma I P(I), \tag{1}$$

The first-order variance $m_2$ and the first-order entropy $m_3$ can be defined by following equations:

$$m_2 = \Sigma (I-m_1)^2 P(I) \text{ and} \tag{2}$$

$$m_3 = -\Sigma P(I) \log_2 P(I). \tag{3}$$

In equations (1) to (3) the summation is performed over different ultrasound intensities I.

The second-order values are preferentially based on the so-called co-occurrence matrices, which are, for example, disclosed in the book "Pattern Recognition" by S. Theodoridis et al., Academic Press, 2003. The second-order values also consider the relative positions of the ultrasound intensities in the M-mode image and are based on the second-order histogram, which can be defined by following equation:

$$P(i, j) = \frac{\text{number of pixel pairs at a given distance with intensities } i \text{ and } j}{\text{total number of possible pairs}}, \tag{4}$$

wherein the variables i and j indicate ultrasound intensities. The given distance is predefined by, for example, calibration measurements, wherein different predefined distances are tried, until the determined property, which depends on the second-order histogram, matches as good as possible a known property of the object. Preferentially, the given distance is one pixel, i.e. pixel pairs at a given distance are preferentially directly neighbored pixels.

The second-order entropy $n_1$, second-order energy $n_2$, the second-order homogeneity $n_3$, the second-order contrast $n_4$, the second-order cluster tendency $n_5$, the second-order cluster shape $n_6$, the second-order correlation $n_7$ and the second-order correlation derivatives $n_8$, $n_9$ can be defined by following equations:

$$n_1 = -\sum P(i,j)\ln P(i,j). \quad (5)$$

$$n_2 = \sum (i-j)^2 P(i,j), \quad (6)$$

$$n_3 = \sum \frac{P(i,j)^2}{1+(i-j)^2}, \quad (7)$$

$$n_4 = \sqrt{\sum P^2(i,j)}, \quad (8)$$

$$n_5 = \sum (i+j-2\mu)^2 P(i,j), \text{ where } \mu = \frac{\sum P(i,j)}{N}, \quad (9)$$

$$n_6 = \sum (i+j-2\mu)^3 P(i,j), \quad (10)$$

$$n_7 = \frac{\sum (i-\mu)(j-\mu)P(i,j)}{\sigma^2}, \text{ where} \quad (11)$$

$$\sigma = \frac{1}{N}\sum (i-\mu)^2 \sum P(i,j),$$

$$n_8 = -\sum P(i,j)\ln\left(\sum_i P(i,j)\sum_j P(i,j)\right) \text{ and} \quad (12)$$

$$n_9 = -\sum \left(\sum_i P(i,j)\sum_j P(i,j)\right)\ln\left(\sum_i P(i,j)\sum_j P(i,j)\right). \quad (13)$$

If not specified otherwise, in equations (5) to (13) the summation is performed over the ultrasound intensities i and j. The logarithms used in equations (5), (12) and (13) can also have another base.

The second-order scatter values provide values being indicative of pattern characteristics of the M-mode image that relates to the spatial arrangement of the pixels of the M-mode image, instead of only the contrast. These second-order statistics describe the randomness, regularities and orientation characteristics of the patterns.

It should be noted that the scatter determination unit 8 does not necessarily determine all of the above mentioned first-order values and second order-values. Preferentially, the scatter determination unit is adapted to determine only the kinds of scatter values, which allow determining the desired property of the object. The kinds of scatter values, which can be used for determining the desired property of the object, can be determined by calibration measurements, wherein several kinds of scatter values are determined, while the property of the object is known. In an embodiment, a calibration measurement revealed that the scatter values $m_1$ to $m_3$ and $n_3$ to $n_9$ can be used for determining whether the tissue is ablated or not ablated. These scatter values are schematically and exemplarily shown in FIGS. 4 to 13. In these figures the respective scatter value is shown in arbitrary units depending on the time in seconds. In all of these figures the transition between non-ablated tissue and ablated tissue is visible between about 60 to 80 seconds.

The scatter determination unit 8 can further be adapted to determine at least one scatter value for a sample window depending on a sum of the ultrasound intensities within the respective sample window and not depending on a histogram. For example, this at least one scatter value can be the sum over all ultrasound intensities within the respective sample window. The at least one scatter value can also be defined by following equation:

$$f = \Sigma I_t I_{t-p}, \quad (14)$$

wherein $I_t$ indicates the ultrasound intensity of a pixel of the M-mode image at the time t and $I_{t-p}$ indicates the ultrasound intensity of a pixel of the M-mode image at the time t–p, wherein p indicates the time between two consecutive heart beats. In equation (14), the summation is performed over all pairs $I_t I_{t-p}$ for which the pixels, which correspond to $I_t$, are located within the respective sample window. The time between two consecutive heartbeats can be determined by an electrocardiograph, which is schematically and exemplarily indicated in FIG. 1 by the box with the reference number 9. In other embodiments, the ablation apparatus may not comprise the electrocardiograph 9 and the time between two consecutive heartbeats may be determined from, for example, the M-mode image.

The ablation apparatus further comprises a property determination unit 15 for determining a property of the object 3 depending on the scatter values determined by the scatter determination unit 8. In this embodiment, the property determination unit 15 is adapted to determine whether a part of the tissue is ablated tissue or non-ablated tissue based on the scatter values as the property of the object. By ablation the perfusion of the tissue can be modified, wherein the modification of the perfusion modifies the scattering of the ultrasound pulse and, thus, the scatter values. The scatter values can therefore be used for determining whether the tissue is ablated or not ablated.

In this embodiment, the property determination unit 15 is adapted to determine for each of the scatter values of a sample window a voting for the tissue being ablated or the tissue being not ablated. For each of these values the voting is performed by comparing the respective value with a predefined threshold value, i.e. for each of the values a binary thresholding is performed, in order to determine for each value a voting. The property determination unit 15 is adapted to determine the final result, i.e. whether the tissue, which corresponds to the respective sample window, is ablated or not ablated, based on the majority of the votings. This means that, if for a sample window more votings for being ablated than for being non-ablated have been determined, the final result is that the tissue, which corresponds to the respective sample window, is ablated and vice versa. The predefined threshold values can be determined by, for example, calibration measurements.

The property determination unit can also be adapted to combine the several scatter values to a multi-dimensional feature vector, i.e. for each sample window, a multi-dimensional feature vector can be defined, wherein the multi-dimensional feature vector can be compared with a predefined threshold vector for determining whether the respective sample window corresponds to ablated tissue or to non-ablated tissue. Also this predefined threshold vector can be determined by, for example, calibration measurements.

The property determination unit can also be adapted to apply a cluster analysis to the sample windows, wherein the sample windows are clustered depending on the multi-dimensional feature vectors, and to assign properties to the clusters of sample windows. For example, the cluster analysis can result in two clusters of sample windows, wherein the property "ablated tissue" is assigned to one of these clusters and the property "non-ablated tissue" is assigned to the other of the clusters. Whether a cluster represents ablated or non-ablated tissue can be determined depending on a comparison with a threshold, wherein, for example, the multi-dimensional feature vectors of a cluster can be averaged for generating an average vector and wherein the average vector of the cluster can be compared with a threshold vector which can be determined by calibration measurements. Thus, the assignment of properties of the object to the sample windows can be performed by thresholding. It is also possible that the cluster analysis is firstly applied before ablation is started, leading to a first group of clusters representing non-ablated tissue. Then, the cluster analysis can continuously be applied, while the ablation procedure is performed. If the cluster analysis leads to new clusters, which do not belong to the first group of clusters, the property "ablated tissue" can be assigned to these new clusters.

Figure 17:
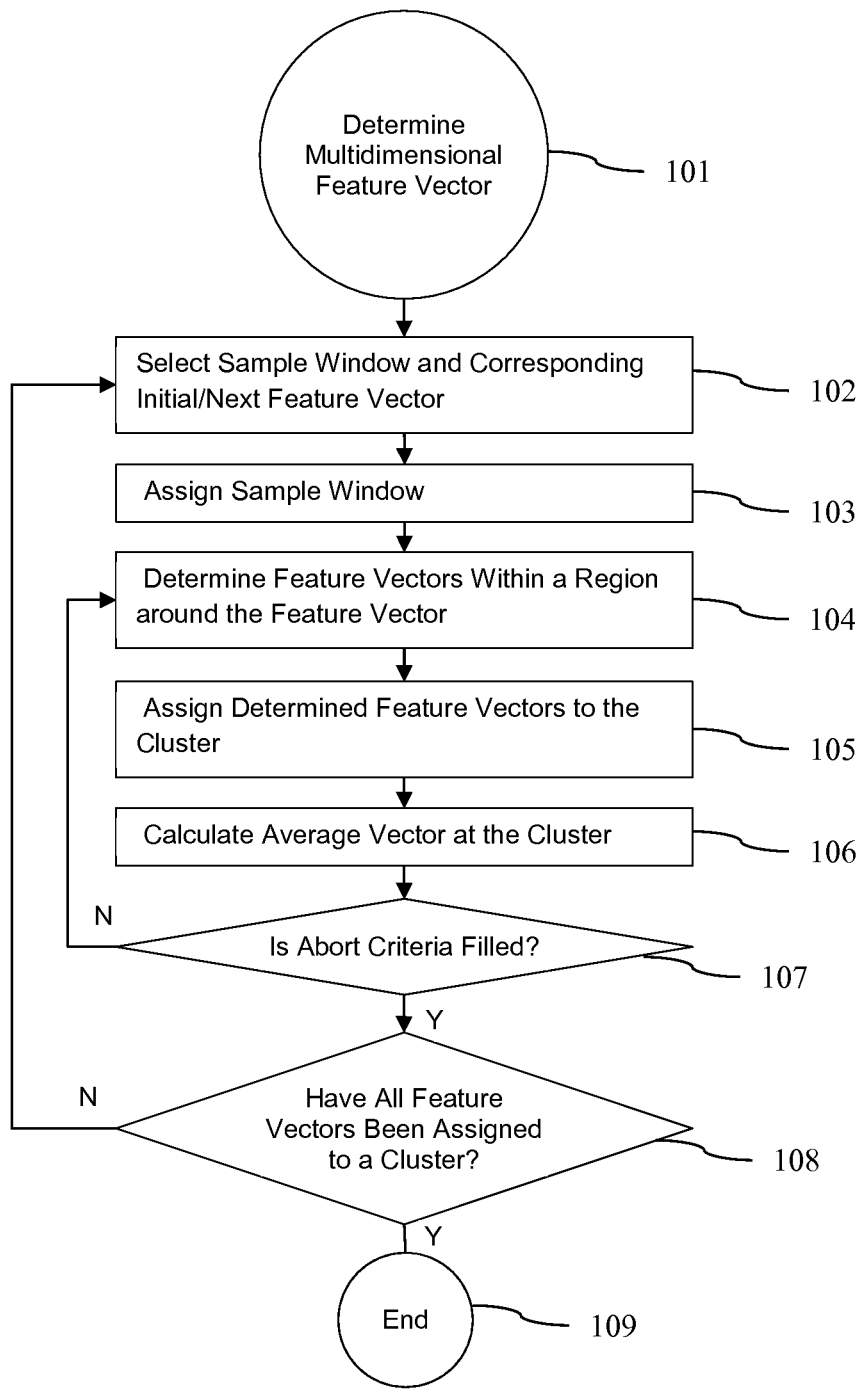
FIGS. 17 and 18 show flowcharts exemplarily illustrating a cluster algorithm.
Figure 18:
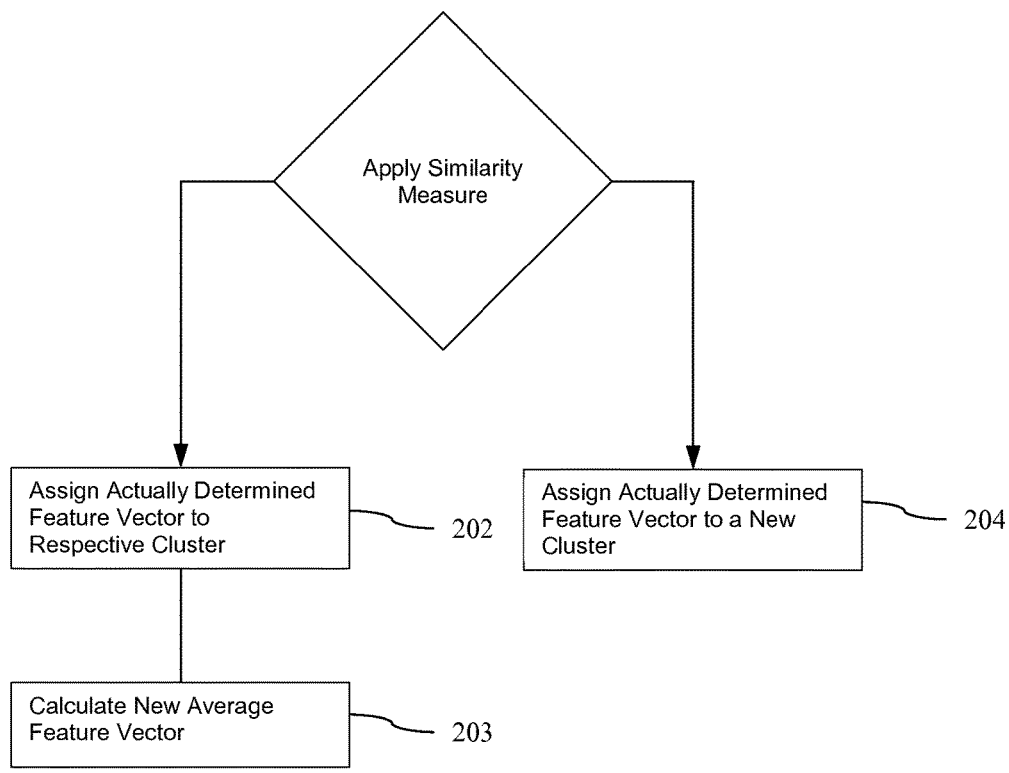

In an embodiment, the property determination unit is adapted to apply following cluster analysis technique for determining which part of the tissue is ablated and which part of the tissue is not ablated. The cluster analysis technique will be described with reference to FIGS. 14 to 18, wherein in FIGS. 14 to 16 the upper part shows an M-mode image and the lower part shows a result of the cluster analysis technique and wherein FIGS. 17 and 18 show flowcharts illustrating several steps of the cluster analysis technique.

The scatter determination unit determines scatter values for several sample windows 131. The sample windows 131 sample the entire M-mode image and are overlapping. The overlapping of the sample windows 131 increases the resolution of the final clustering result. The sample windows correspond to certain depth ranges and certain time ranges. The sample windows 131 can have the same width and the same length, or the width and the length of the sample windows can be different. Moreover, the M-mode image can be sampled by different sample windows having different sizes and/or different shapes. Preferentially, the width of the window covers at least one heart beat cycle, wherein the sample windows can be aligned with respect to the heart beat. For example, each sample window can start at the same time shift with respect to the respective contraction cycle. In an embodiment, the size of the sample windows in the depth direction is about 0.2 mm.

Figure 14:
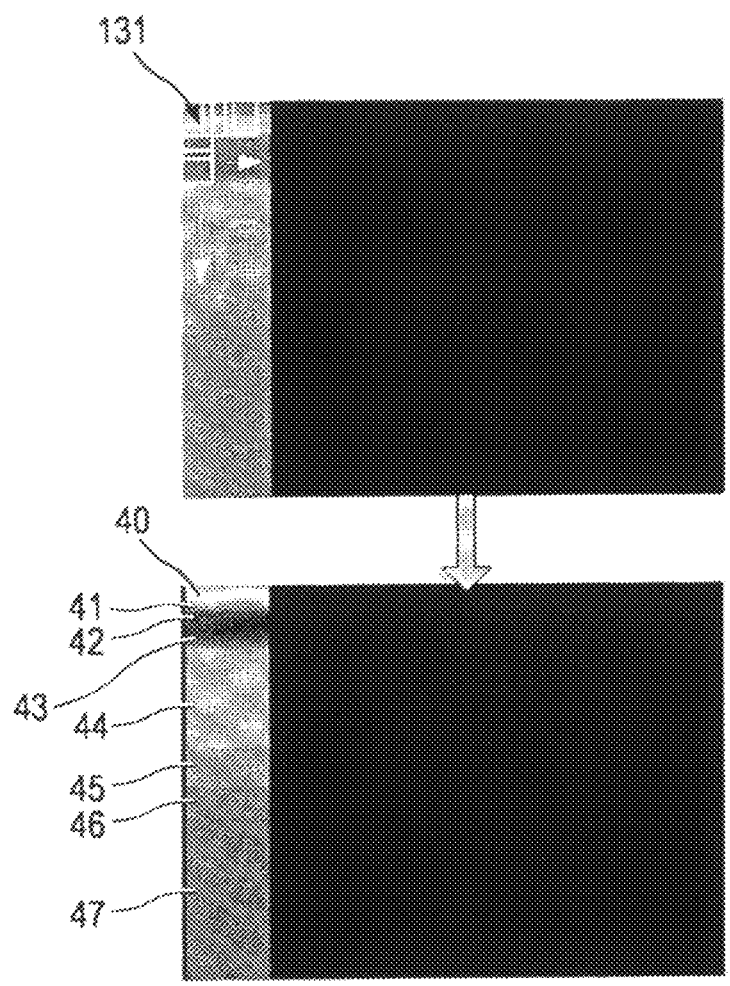
FIGS. 14 to 16 show exemplarily several M-mode images of the object and corresponding cluster results.

A first cluster analysis technique is performed before ablation is started, wherein the corresponding M-mode image is shown in the upper part of FIG. 14. This first cluster analysis technique will be described in the following with reference to the flowchart shown in FIG. 17.

The first cluster analysis technique is initialized in step 101 by providing the M-mode image showing the tissue before ablation is started, by sampling the M-mode image with sample windows and by determining for each of the sample windows a multi-dimensional feature vector comprising scatter values.

In step 102, a sample window and, thus, a corresponding initial feature vector are selected. This selection can be performed randomly. In step 103, the initial feature vector and, thus, the selected sample window are assigned to a first cluster. In step 104, it is determined which feature vectors are arranged within a region around the initial feature vector in the multi-dimensional feature vector space containing the multi-dimensional feature vectors. The region is preferentially a circle, if the feature vector is a two-dimensional vector, or a hypersphere, if the feature vector has a dimension being larger than two. The size of the region can be determined by calibration measurements.

In step 105, the determined feature vectors, which are located within the region around the initial feature vector, are assigned to the first cluster, and, in step 106, the feature vectors within the first cluster are averaged for calculating an average vector of the first cluster. In step 107, it is determined whether an abort criterion is fulfilled. The abort criterion is, for example, whether a predefined number of iterations has already been reached or whether a converging criterion has been met. The converging criterion is, for example, that the difference between the initial feature vector and the average feature vector or the difference between the actually determined average feature vector and a previously determined average feature vector is below a predefined threshold. If the abort criterion is not fulfilled, the cluster analysis performs steps 104 to 107 again, wherein now instead of the initial feature vector the actually determined average feature vector is used, i.e. in step 104 feature vectors are determined within a region around the actually determined average feature vector, in step 105 the feature vectors in the region around the actual average vector, which have not already been assigned to the first cluster, are assigned to the first cluster, and in step 106 a new average feature vector is calculated by averaging the feature vectors of the first cluster.

If in step 107 the abort criterion is fulfilled, the first cluster has been determined and the method continues with step 108. In 108 it is determined whether all feature vectors and, thus, all sample windows have been assigned to a cluster. If not all feature vectors have been assigned to a cluster, steps 102 to 107 are performed based on the remaining feature vectors, which have not been assigned to a cluster, in order to determine a further cluster. Steps 102 to 108 are therefore performed, until all feature vectors and, thus, sample windows have been assigned to a cluster. After all feature vectors have been assigned to a cluster, the first cluster analysis technique ends in step 109. Since the first cluster analysis technique is applied to an M-mode image, which shows the tissue before ablation is started, the clusters, which have been determined by performing steps 101 to 109, correspond to non-ablated tissue.

Figure 15:
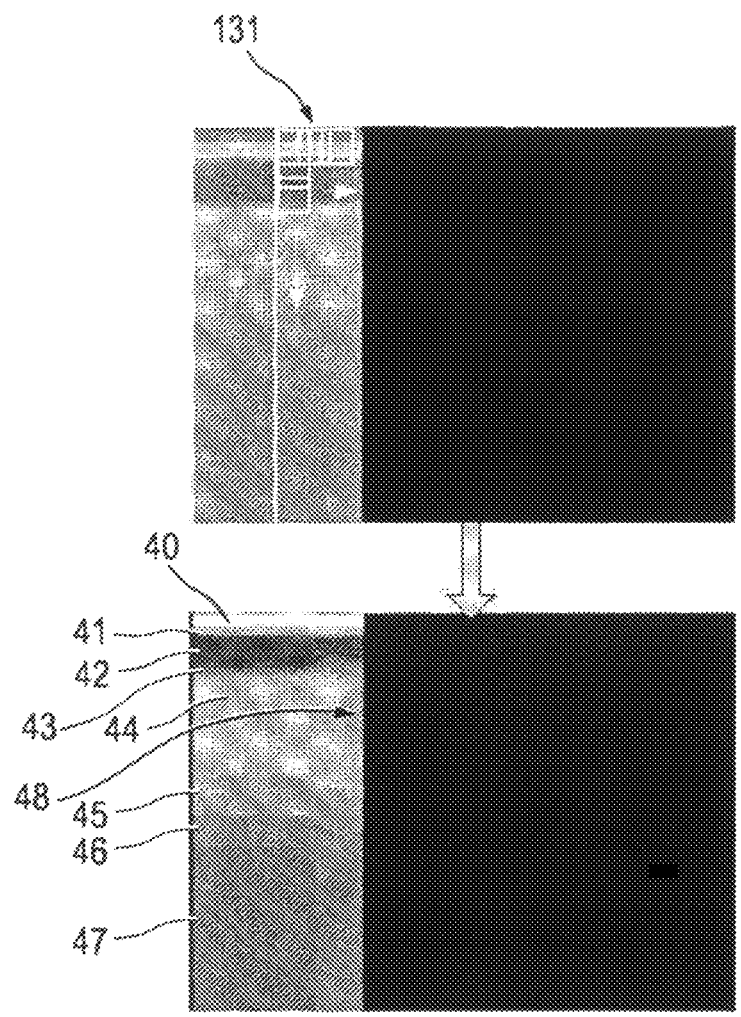
Figure 16:
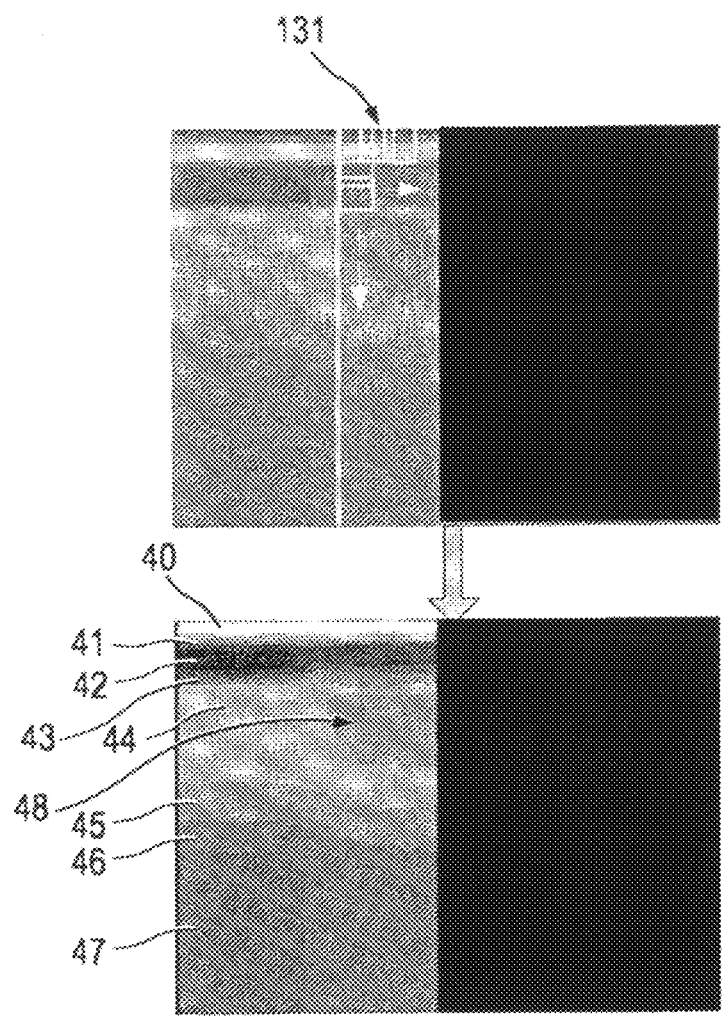

FIGS. 15 and 16 show M-mode images which illustrate the tissue not only before ablation is started, but also after ablation has been started. While the ablation is performed, the ultrasound signal is continuously generated and sampled. Thus, sample windows are continuously acquired and for each sample window a feature vector is calculated, i.e., continuously feature vectors are determined, wherein the continuously newly determined feature vectors are clustered in accordance with a second cluster analysis technique, which will be described in the following with reference to the flowchart shown in FIG. 18.

In step 201, a similarity measure is applied to the actually determined feature vector and to each of the average vectors of the already determined clusters. The similarity measure is, for example, the absolute difference between the actually determined feature vector and the respective average feature vector, wherein, if this absolute difference is below a predefined threshold, the actually determined feature vector is regarded as being similar to the respective average feature vector. If the actually determined feature vector is similar to an average feature vector of a certain cluster, the actually determined feature vector is assigned to the certain cluster in step 202, wherein in step 203 a new average feature vector is calculated for this certain cluster taking into account the newly assigned actually determined feature vector.

If, in step 201, it is determined that the actually determined feature vector is not similar to any of the average feature vectors of the existing clusters, the method continuous with step 204. In step 204, the actually determined feature vector, which could not be assigned to an existing cluster, defines a new cluster and the actually determined feature vector is defined as the average feature vector of this new cluster.

As it can be exemplarily seen in the lower part of FIG. 14, before ablation is started, several clusters 40 . . . 47 are present, which can belong to different structures of non-ablated tissue. In the lower parts of FIGS. 15 and 16 a new cluster 48 can be seen, which is generated, after ablation has been started. The property determination unit assigns this new cluster 48 therefore to "ablated tissue" and the other clusters 40 . . . 47 to "non-ablated".

The ablation apparatus 1 further comprises a display 10 for showing the determined property. In particular, the display 10 is adapted to show which parts of the tissue are ablated and which parts of the tissue are not ablated.

The property determination unit is preferentially further adapted to determine an ablation depth depending on the determined ablated parts and non-ablated parts. Since from the M-mode image the positions of the ablated parts and the non-ablated parts are known, the ablation depth, i.e. the depth to which the tissue has been ablated starting from an outer surface of the tissue, can easily be determined. The display 10 can also be adapted to show this ablation depth.

The ablation apparatus 1 further comprises a heart wall thickness determination unit 54 for determining the thickness of a heart wall depending on an A-line of the M-mode image. The A-line is defined by the ultrasound intensities of the M-mode image, which represent amplitudes of the ultrasound signal, at a fixed time t. Such an A-line 61 is schematically and exemplarily shown in FIG. 19, in which the amplitude a of the A-line is shown in arbitrary units depending on the depths d in arbitrary units.

The regions of the A-line 61 denoted by 62 and 63 correspond to front and back surfaces of the heart wall. The region 64 is directly generated by the ultrasound pulse.

Figure 19:
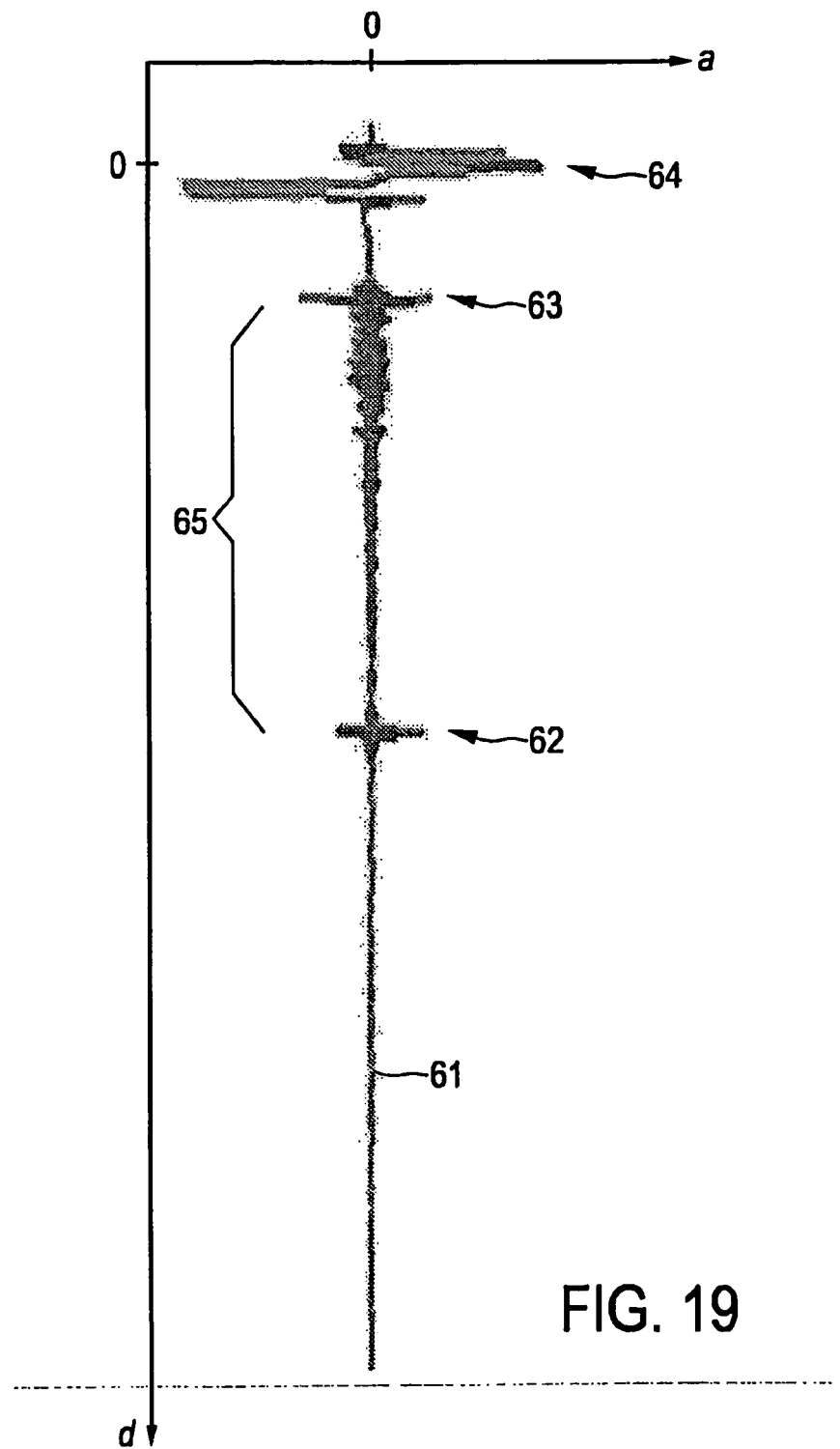
FIG. 19 shows an A-line of an M-mode image.

The A-line 61 shown in FIG. 19 allows determining the position of the front and back surfaces 62, 63 with respect to the position of the ultrasound transducer 18 that emits the ultrasound pulse and receives the echoes. The first measured amplitude in the region 64 defines the position of the ultrasound unit. Region 64 is followed by a region comprising an amplitude being substantially zero and after a while the amplitude increases again in region 63 marking the first reflection at the object, i.e. marking the front surface of the object. A region 65 comprising small amplitudes that correspond to reflections within the tissue of the heart wall follows, and then in region 62 the amplitude increases again significantly, thereby marking the back surface of the heart wall. Thus, the A-line 61 allows determining the positions of the front and back surfaces based on the regions 62 and 63. The heart wall thickness determination unit is preferentially adapted to determine the position of the increasing amplitude in region 63 after a region comprising an amplitude value being substantially zero as the position of the front surface of the object. Then, the amplitude substantially decreases in region 65 and the position of the next significant increase of the amplitude (region 62) is determined as the position of the back surface of the heart wall. In other words, after the ring down of the transducer of the ultrasound unit in region 64 a "quiet period" ensues. This quiet period is subsequently terminated by a reflection in region 63 that is associated to the front surface. After this reflection in the region 63 a period 65 occurs that is marked by fast and small temperature changes in the ultrasound intensity. In particular, the envelope of the signal in the period 65 tends to have an exponential decrease in intensity. At the end of the period 65 again a strong reflection is observed in the region 62 that is associated to the back surface. Threshold values can predefined, in particular relative threshold values can be predefined, wherein the front surface is detected, if a reflection after the "quiet period" exceeds the respective predefined threshold and wherein the back surface is detected, if at the end of period 65 the signal exceeds the respective threshold. The thresholds can be predefined by calibration measurements with walls having known front surface and back surface positions.

In an embodiment, the property determination unit can also be adapted to determine the degree of transmurality of a heart wall depending on the determined ablation depth and the determined positions of the front surface and the back surface of the heart wall.

The ablation apparatus 1 further comprises a control unit 11 for controlling the ablation of the object depending on the property of the object, which is determined by the property determination unit. In particular, the control unit 11 can be adapted to control the ablation of tissue of the object depending on the determined ablated parts and non-ablated parts of the tissue of the object. For example, if a certain part of the tissue of the object should be ablated, the control unit 11 can control the ablation of the tissue of the object such that the RF energy is applied, until the respective part is completely ablated. For performing this control of the ablation procedure, the ablated parts of the tissue and the non-ablated part of the tissue are preferentially determined in realtime. The control unit 11 can also be adapted to control the ablation of a heart wall depending on the degree of transmurality. In particular, the control unit 11 can be adapted to control the ablation such that the heart wall is completely ablated, without ablating the underlying tissue, i.e. the control unit can be adapted to control the ablation apparatus such that a transmurality of 100 percent is reached.

The units and elements of the ablation apparatus 1, which are used for determining the property of the object, in particular, for determining ablated parts and non-ablated parts of the object, form a property determining apparatus which is integrated into the ablation apparatus. However, the property determining apparatus can also be a separate apparatus, which is not integrated into an ablation apparatus.

Figure 20:
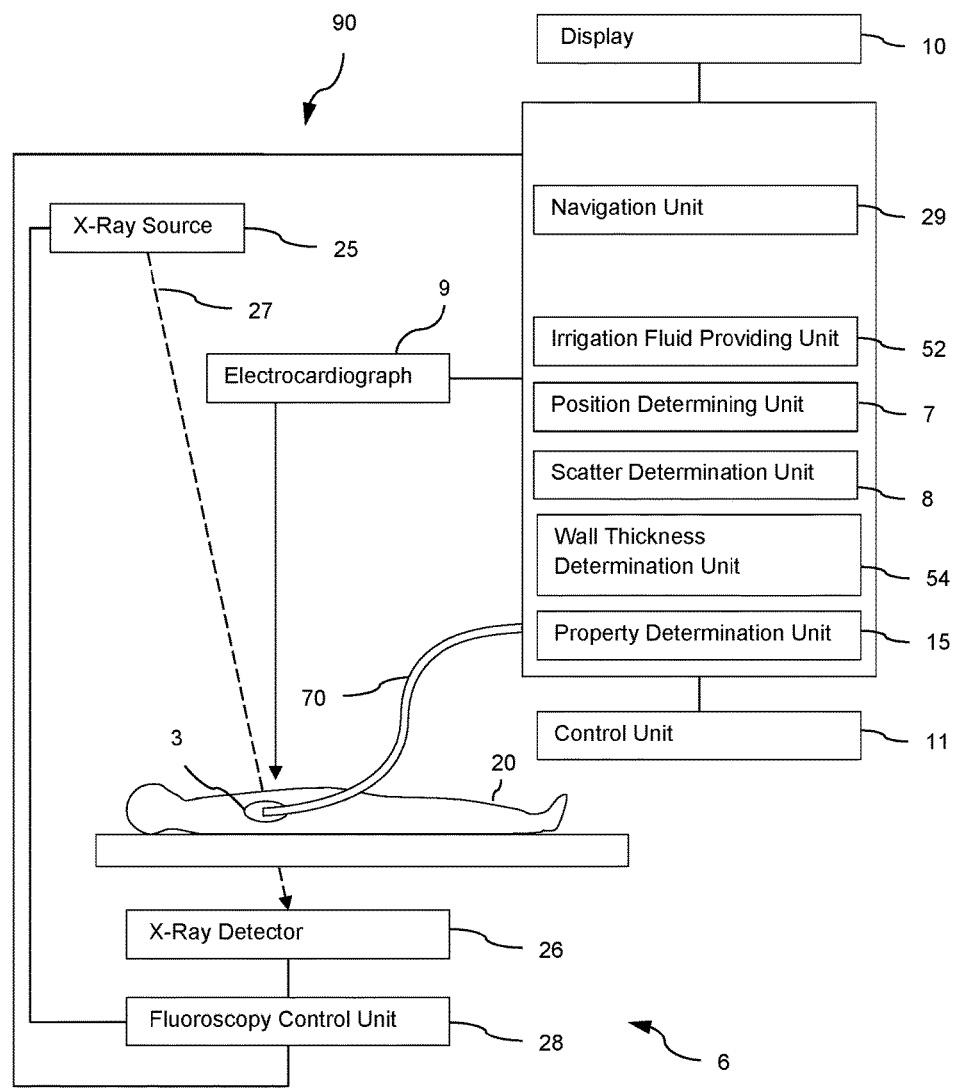
FIG. 20 shows schematically and exemplarily an embodiment of a property determining apparatus for determining a property of an object.

A separate property determining apparatus is schematically and exemplarily shown in FIG. 20. The elements and units of the property determining apparatus 90 shown in FIG. 20 are similar to the corresponding elements and units described above with reference to FIG. 1 and are denoted by similar reference numbers. For a detailed description of the property determining apparatus 90 reference is therefore made to the above description of FIG. 1.

Figure 21:
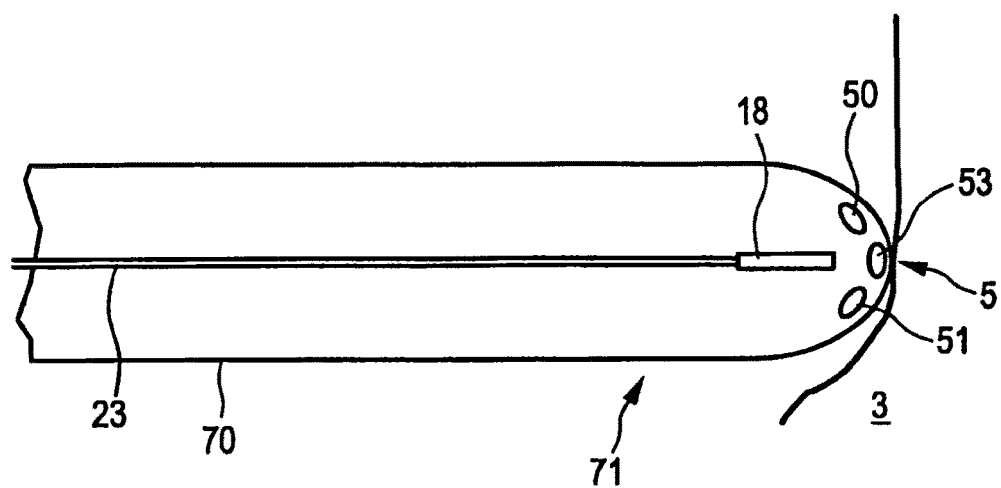
FIG. 21 shows schematically and exemplarily an embodiment of a tip of a catheter of the property determining apparatus.

FIG. 21 shows schematically and exemplarily an embodiment of a catheter tip 71 of the catheter 70 of the property determining apparatus 90. The elements and units of the catheter tip 71 of the catheter 70 of the property determining apparatus 90 are similar to the corresponding elements and units described above with reference to FIG. 2 and are therefore denoted by similar reference numbers. For a detailed description of these elements and units reference is therefore made to the description provided above with reference to FIG. 2. In contrast to the catheter tip of the ablation apparatus, the catheter tip of the property determining apparatus 90 does not comprise an ablation electrode.

Figure 22:
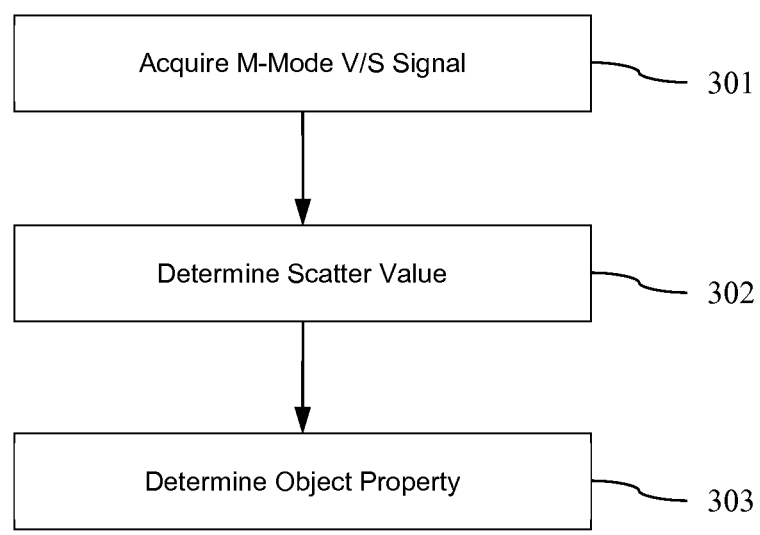
FIG. 22 shows a flowchart exemplarily illustrating an embodiment of a property determining method for determining a property of an object.

In the following an embodiment of a property determining method will exemplarily be described with reference to a flowchart shown in FIG. 22.

In step 301, an ultrasound signal is provided by sending an ultrasound pulse out to the object 3, receiving echo series from the object 3, and generating the ultrasound signal depending on the received echo series. The ultrasound signal being an M-mode image is provided by the ultrasound transducer 18. In step 302, at least one scatter value being indicative of a scatter of the ultrasound pulse by fluid of the object 3 is determined depending on the provided ultrasound signal. In step 303, depending on the one or several scatter values properties of the object, in particular, ablated parts of the object and non-ablated parts of the object, are determined.

Figure 23:
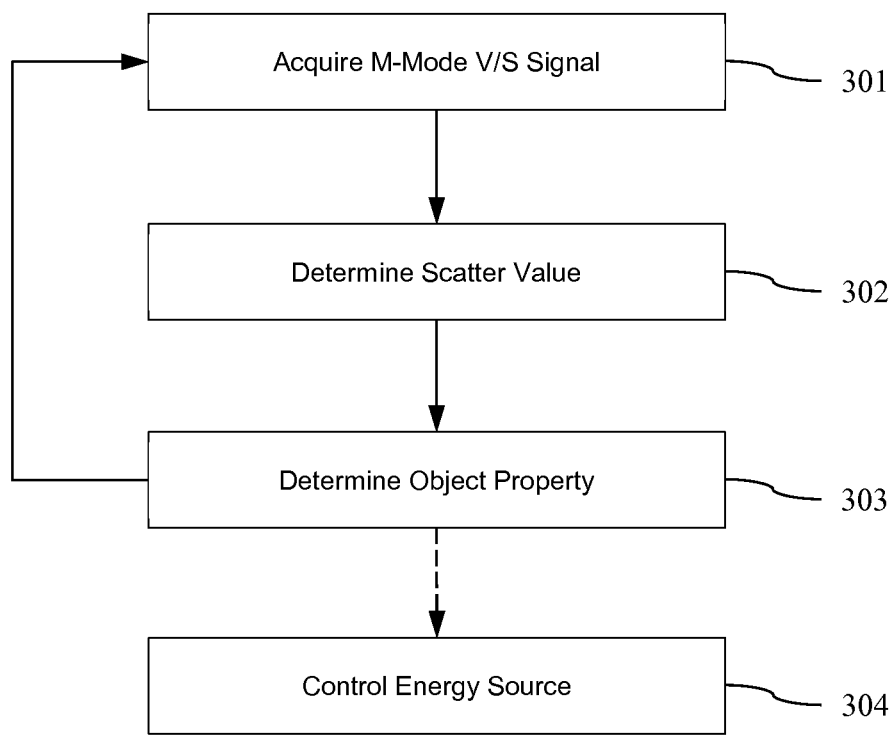
FIG. 23 shows a flowchart exemplarily illustrating an ablation method for ablating an object.

In the following an embodiment of an ablation method for ablating an object will exemplarily be described with reference to a flowchart show in FIG. 23. In step 301, an ultrasound signal is provided, in step 302, at least one scatter value is determined based on the provided ultrasound signal; and, in step 303, a property of the object is determined depending on the at least one scatter value. Steps 301 to 303 are similar to the steps described above with reference to FIG. 22 and are performed in a loop, in order to continuously determine which part of the object is ablated and which part of the object is not ablated. This ablation information is provided to the control unit 11 of the ablation apparatus 1, wherein the ablation of the object in step 304, in particular, the application of RF energy via the ablation electrode 4, is controlled by controlling the energy source 24 depending on the determined ablation information. Thus, continuously ablation information is determined and used for controlling the ablation procedure.

One major drawback in known catheter ablation procedures for cardiac arrhythmias is the lack of adequate information on the lesion quality while it is being created. Furthermore, by using known methods it is very difficult to find back old lesions in redo ablation procedures. Currently, the therapist relies on his own expertise to determine the optimal parameters for ablation, such as power, temperature, and duration. However, these settings vary largely, for example, due to intra and inter-patient differences of, for example, thickness of the local heart wall, local cooling by blood flow, contact between catheter and tissue, et cetera.

In the prior art, two major therapy-related problems result from either the under-heating or the over-heating of the site. In the case of under-heating, the tissue is not sufficiently coagulated to form the arrhythmia-blocking lesion desired by the therapist. This can lead to persistent or recurring symptoms in the patient, and the requirement for subsequent treatments, longer periods of hospitalization, and greater risks of stroke and embolism. The other extreme, overheating, either causes rupturing of the tissue at the treatment site, releasing potentially life-threatening particles into the blood stream, or causes damage to neighboring organs and tissues.

The ablation apparatus in accordance with the invention provides an improved control. It provides feedback of the lesion development in the tissue, can provide information about the depth of the lesion with respect to the thickness of the tissue at the treatment site, and can prevent injury and death from under-heating and overheating in catheter ablation procedures.

During ablation vascular structures and thus capillary perfusion are generally completely destroyed by coagulation necrosis. In contrast, capillary perfusion with blood cells supplies healthy tissue, which has not been ablated, with oxygen and metabolites. Ablated tissue comprises therefore generally no capillary perfusion or the capillary perfusion is at least strongly reduced and non-ablated tissue comprises a normal capillary perfusion, which is generally not reduced. The at least one scatter value is preferentially indicative of a scatter of the ultrasound pulse by the cells of the blood which perfuses the tissue and is therefore also indicative of ablation information, in particular, whether the tissue is ablated tissue or non-ablated tissue. Thus, the property determination unit can determine whether tissue is ablated tissue or non-ablated tissue based on the at least one scatter value as described above in more detail.

As already mentioned above, the motion of (red) blood cells contributes to the scattering of ultrasound, in particular at higher ultrasound (US) frequencies (>10 MHz). Therefore, ablation-induced change in the motion of the blood cells either due to change in flow rate or complete lack of motion due to destroyed vasculature, affects the scattering of US. This feature can be used as a marker for tissue damage.

In an embodiment, the property determination unit is adapted to identify blood vessels. Since the at least one scatter value can be indicative of a scattering of the ultrasound pulse by blood cells, the property determination unit can be adapted to identify blood vessels, in particular, arteries or veins, depending on the at least one scatter value. For example, by calibration measurements it can be determined which scatter values correspond to blood vessels and the property determination unit can identify a blood vessel, if actually a scatter value is determined, which corresponds, as determined by calibration, to a blood vessel. The control unit of the ablation apparatus can be adapted such that it generates an alarm on the display or on another output unit like an acoustical output unit, if the property determination unit identifies a blood vessel at a location, at which an ablation procedure should be started or continued. In this way, the physician can be notified, when an ablation electrode is positioned on top or very close to a blood vessel, and the application of an ablation procedure on a blood vessel can be avoided. An application of an ablation procedure on a blood vessel should be avoided, because this can cause, for example, ischemia.

The ablation apparatus and the property determining apparatus provide an automatic way to analyze and quantify the scattering pattern change for blood-perfused and non-blood-perfused tissues. As previously mentioned, this pattern difference provides important information for distinguishing healthy cardiac tissue before ablation and coagulated ablated tissue due to ablation. The pattern difference is preferentially based on the statistical analysis of the texture properties of realtime M-mode ultrasound images, especially on the second-order statistical properties which give a clear distinction between the two conditions. This enables distinguishing healthy and coagulated tissue preferentially only based on statistical analysis, and can therefore be used for lesion monitoring purposes, in particular, for controlling the lesion depth, during and/or after ablation.

The at least one scatter value is preferentially determined from ultrasound raw data, because it retains high-frequency information which is used for characterizing the scattering pattern. Thus, the ultrasound signal, which is used for determining the at least one scatter value, is preferentially represented by ultrasound raw data, which have not been processed, for example, which have not been filtered.

Although in the above described embodiments scatter values are determined based on, for example, first-order and second-order histograms, a scatter value can also be determined based on other texture-based analysis which may include higher-order statistics. For example, a Gabor filtering approach, in which certain frequency bands may be able to capture the major differences between ablated tissue and non-ablated tissue, may be used.

Although in the above described embodiments the ultrasound transducer is integrated into a catheter, the ultrasound transducer can also be integrated into, for example, a needle.

Referring again to FIG. 1, the irrigation fluid providing unit 52 can be adapted to add a vasodilator like isoproterenol in the irrigation fluid. When a bolus of the vasodilator is applied just before the ablation starts, the local perfusion of the target location increases. In this way, the difference in blood-induced ultrasound scattering before and after ablation can be enhanced, thus facilitating the analysis, i.e. facilitating the distinguishing of ablated tissue from non-ablated tissue based on the at least one scatter value by the property determination unit.

Although in an above described embodiment the property determining apparatus is integrated into an ablation apparatus, in other embodiments the property determining apparatus can also be integrated into another object influencing apparatus, for example, into a biopsy apparatus for performing a biopsy. The biopsy apparatus comprises a biopsy needle, wherein an ultrasound transducer can be integrated into the tip of the biopsy needle. The biopsy apparatus can be used in, for example, oncology and for distinguishing ablated tumors from non-ablated tumors. Typically, a tumor is characterized by a dense core of coagulated tissue surrounded by hyper-perfused tissue. This surrounding tissue is the target tissue to take a biopsy from. Ultrasound pulses can be scattered by the surrounding hyper-perfused tissue, and at least one scatter value can be determined based on the resulting ultrasound signal. Based on this at least one scatter value it can be determined which part of the tumor is the dense core of coagulated tissue and which part of the tumor is the hyper-perfused tissue, from which a biopsy has to be taken.

Figure 24:
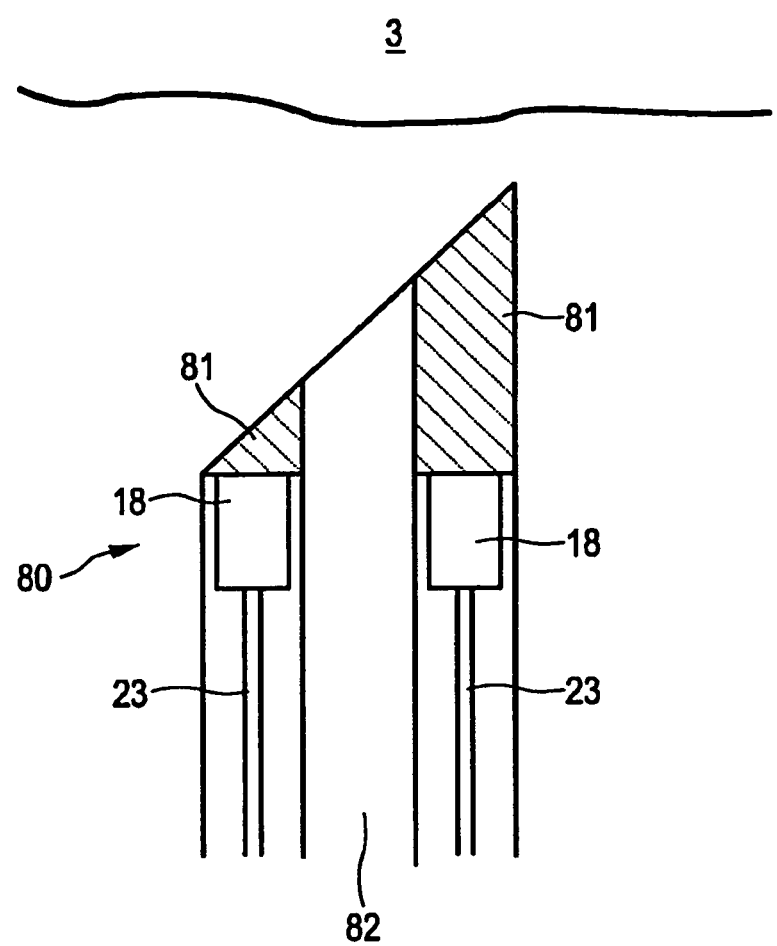
FIG. 24 shows schematically and exemplarily an embodiment of a tip of a biopsy needle.

FIG. 24 shows schematically and exemplarily an embodiment of a tip 80 of a biopsy needle. The biopsy needle comprises a plurality of ultrasound transducers 18 located in an outer region of the tip 80 of the biopsy needle. This outer region surrounds a central lumen 82. The central lumen is used for introducing a biopsy instrument for taking a part of the tissue 3 and for transferring this part to the outside of the person. The ultrasound transducers 18 provide ultrasound signals by sending an ultrasound pulse out to the tissue, receiving echo series from the tissue, and generating the ultrasound signal depending on the received echo series. The ultrasound signal is transmitted to a scatter determination unit via electrical connections 23. The scatter determination unit determines at least one scatter value being indicative of a scatter of the ultrasound pulse by the fluid within the tissue, wherein the at least one scatter value is determined depending on the ultrasound signal, and a property determination unit determines a property of the tissue depending on the at least one scatter value as described above with reference to FIGS. 1 and 2. In particular, the property determination unit determines which part of a tumor is a dense core of coagulated tissue, which, regarding perfusion, corresponds to ablated tissue, and which part of a tumor is hyper-perfused tissue, from which a biopsy has to be taken and which, regarding perfusion, corresponds to non-ablated tissue. The biopsy apparatus preferentially further comprises the image providing unit 2, the localization unit 6, 7 and the navigation unit 29 described above with reference to FIG. 1. Between the distal end of the tip of the biopsy needle and the ultrasound transducers 18 an acoustically transparent material 81 like polymethylpentene is provided for defining an acoustical path between the ultrasound transducers 18 and the outside of the biopsy needle.

Although in an above described embodiment the positions of the front and back surfaces of the heart wall are determined from the amplitude of an A-line, in other embodiments these positions can be determined in other ways. For example, the positions of the front and back surfaces of the heart wall can be determined based on a spectrum analysis of the A-line over depth.

The ablation apparatus and the property determining apparatus can be used in tissue imaging during treatment of, for example, cardiac arrhythmias and tumor ablation. In these procedures, it is desired to follow the progression of lesion formation during the procedure.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

Determinations like the determination of a scatter value and of a property of the object performed by one or several units or devices can be performed by any other number of units or devices. For example, the determination of a scatter value and the determination of a property of the object can be performed by a single unit or by any other number of different units. The determinations and/or the control of the ablation apparatus in accordance with the ablation method and/or the control of the property determining apparatus in accordance with the property determining method can be implemented as program code means of a computer program and/or as dedicated hardware.

A single unit or device may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention relates to a property determining apparatus for determining a property of an object, which is preferentially a heart. An ultrasound signal providing unit provides an ultrasound signal of the object and a scatter determination unit determines at least one scatter value being indicative of a scatter of the ultrasound pulse by a fluid perfusing the object depending on the ultrasound signal. A property determination unit determines a property of the object depending on the at least one scatter value. In contrast to tissue damage detection methods based on bubble formation, an object property related to perfusion, like whether tissue is ablated or non-ablated, can relatively directly be determined based on the scatter of the ultrasound pulse by the fluid, thereby increasing the accuracy of determining a property of the object.

The invention claimed is:

1. Property determining apparatus for determining a property of an object, wherein the property determining apparatus comprises:
   an ultrasound signal providing unit (18) for providing an ultrasound signal produced by
      sending an ultrasound pulse out to the object,
      receiving echo series from the object, and
      generating the ultrasound signal depending on the received echo series, a scatter determination unit (8) for determining at least one scatter value being indicative of a scatter of the ultrasound pulse by a fluid perfusing the object, wherein the scatter determination unit (8) is adapted to determine the at least one scatter value based on a histogram of ultrasound intensities of the ultrasound signal, a property determination unit (15) for determining a property of the object depending on the at least one scatter value.

2. The property determining apparatus as defined in claim 1, wherein the object (3) is a biological object comprising tissue and wherein the property determination unit (15) is adapted to determine whether a part of the tissue comprises ablated tissue or non-ablated tissue based on the at least one scatter value as the property of the object.

3. The property determining apparatus as defined in claim 1, wherein the provided ultrasound signal represents the scattering by the fluid at at least one of a) different depths within the object and b) different times, wherein the ultrasound signal is sampled by sample windows corresponding to the at least one of a) different depths and b) different times, wherein the scatter value determination unit (8) is adapted to determine the at least one scatter value for each one of the sample windows, wherein for each respective one of the sample windows, the at least one scatter value is determined based on a part of the ultrasound signal which corresponds to the respective sample window and wherein the property determination unit is adapted to determine the property for the respective sample window based on the at least one scatter value determined for the respective sample window.

4. The property determining apparatus as defined in claim 3, wherein each of the sample windows corresponds to several ultrasound intensities of the ultrasound signal and wherein the scatter determination unit is adapted to determine the at least one scatter value for each sample window, wherein the histogram comprises the ultrasound intensities within the respective sample window.

5. The property determining apparatus as defined in claim 4, wherein the histogram is at least one of a first-order histogram and a second-order histogram.

6. The property determining apparatus as defined in claim 5, wherein the scatter value is at least one of: a first-order mean of the first-order histogram, a first-order variance of the first-order histogram, a first-order entropy of the first-order histogram, a second-order entropy of the second-order histogram, a second-order energy of the second-order histogram, a second-order homogeneity of the second-order histogram, a second-order contrast of the second-order histogram, a second-order cluster tendency of the second-order histogram, a second-order shape of the second-order histogram, a second-order correlation of the second-order histogram and a second-order correlation derivative of the second-order histogram.

7. The property determining apparatus as defined in claim 3, wherein the property determination unit is further adapted to apply a duster analysis to the sample windows, wherein the sample windows are clustered depending on the at least one scatter value determined for each respective sample window, and the property determination unit is further adapted to assign the property to each of the clusters of sample windows.

8. The property determining apparatus as defined in claim 1, wherein the ultrasound signal providing unit (18) is adapted to provide the ultrasound pulses at a frequency being larger than 10 MHz.

9. The property determining apparatus as defined in claim 1, wherein the ultrasound signal providing unit (18) is an ultrasound transducer integrated into a catheter or a needle.

10. The property determining apparatus as defined in claim 1, wherein said at least one scatter value is determined independently of heating the object.

11. An object influencing apparatus for influencing an object, the object influencing apparatus comprising an object influencing unit (4, 23, 24) for influencing the object, the property determining apparatus as defined in claim 1, and a control unit adapted for controlling the object influencing apparatus depending on the property determined by the property determination apparatus.

12. A property determining method for determining a property of an object, wherein the property determining method comprises:
providing by an ultrasound transducer, an ultrasound signal produced by
sending an ultrasound pulse out to the object,
receiving echo series from the object, and
generating the ultrasound signal depending on the received echo series,
determining, in a processor executing a program code means, at least one scatter value being indicative of a scatter of the ultrasound pulse by a fluid perfusing the object, wherein the at least one scatter value is based on a histogram of ultrasound intensities of the ultrasound signal,
determining, in a processor executing a program code means, a property of the object depending on the at least one scatter value.

13. The method of claim 12, further comprising the step of influencing the object based on the determined property.

* * * * *